(12) United States Patent
Cornelius et al.

(10) Patent No.: US 9,072,591 B2
(45) Date of Patent: *Jul. 7, 2015

(54) MICRO-CURRENT SENSING AUTO-ADJUSTING HEATER SYSTEM FOR EYE-SHIELD

(71) Applicant: Abominable Labs, LLC, Tigard, OR (US)

(72) Inventors: Jack C. Cornelius, Lake Oswego, OR (US); Vincent O'Malley, Portland, OR (US)

(73) Assignee: Abominable Labs, LLC, Lake Oswego, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/556,128

(22) Filed: Nov. 29, 2014

(65) Prior Publication Data

US 2015/0121610 A1  May 7, 2015

Related U.S. Application Data

(63) Continuation-in-part of application No. 14/040,683, filed on Sep. 29, 2013, which is a continuation of application No. 13/397,691, filed on Feb. 16, 2012, now Pat. No. 8,566,962.

(51) Int. Cl.
*A61F 9/04* (2006.01)
*A61F 9/02* (2006.01)
(Continued)

(52) U.S. Cl.
CPC *A61F 9/029* (2013.01); *H05B 1/02* (2013.01); *A61F 9/04* (2013.01); *A42B 3/245* (2013.01); *A61F 9/022* (2013.01); *A61F 9/028* (2013.01);
(Continued)

(58) Field of Classification Search
CPC ........... A61F 9/04; A61F 9/029; A61F 9/028; A42B 3/228; A63B 71/10; A63B 33/002; G02C 7/16; G02C 5/00; G02C 11/08; G02C 11/00; H05B 2203/036
USPC ............... 2/15, 6.3, 425, 426, 427, 432, 435; 219/203, 211; 351/41, 62, 158; 359/512
See application file for complete search history.

(56) References Cited

U.S. PATENT DOCUMENTS 3,160,735 A * 12/1964 Aufricht ........................... 2/435
4,357,524 A    11/1982 Apfelbeck et al.
(Continued)

FOREIGN PATENT DOCUMENTS

CA    2381876    *  3/2003 ................ A61F 9/04

*Primary Examiner* — Tejash Patel
(74) *Attorney, Agent, or Firm* — Howard Russell

(57) ABSTRACT

Eye-shield condensation prevention system for use in a ski goggle, dive mask, medical or testing face shield or the like, that prevents undesirable hot spots on the eye-shield and maintains constant heat, with the ability to compensate for variations in resistance encountered from one eye-shield region to another, and/or one eye-shield to another, comprising a power source, a pulse-width modulator, a microcomputer, a heating element, and a sensing circuit. The microcomputer uses the sensing circuit to sense voltage and determine a value of resistance of the heating element. The microcomputer then uses this value to adjust the duty cycle of the pulse-width modulator, and may employ a two-dimensional table in assisting calculation. Multiple pulse-width modulators may be employed that correspond to a plurality of eye-shield regions and a corresponding plurality of heating elements.

4 Claims, 10 Drawing Sheets

(51) Int. Cl.
*H05B 1/02* (2006.01)
*A42B 3/24* (2006.01)
*B63C 11/12* (2006.01)
*G02C 11/08* (2006.01)
*H05B 1/00* (2006.01)
*B63C 11/28* (2006.01)

(52) U.S. Cl.
CPC ................ *B63C 11/12* (2013.01); *B63C 11/28* (2013.01); *G02C 11/08* (2013.01); *H05B 1/00* (2013.01)

(56) References Cited

U.S. PATENT DOCUMENTS

| | | |
|---|---|---|
| 4,584,721 A | 4/1986 | Yamamoto |
| 4,868,929 A | 9/1989 | Curcio |
| 4,942,629 A | 7/1990 | Stadlmann |
| 5,105,067 A | 4/1992 | Brekkestran et al. |
| 5,319,397 A * | 6/1994 | Ryden ............... 351/62 |
| 5,351,339 A | 10/1994 | Reuber et al. |
| 5,363,153 A * | 11/1994 | Bailiff .............. 351/78 |
| 5,459,533 A | 10/1995 | McCooeye et al. |
| 5,471,036 A * | 11/1995 | Sperbeck ............ 219/522 |
| 5,778,689 A | 7/1998 | Beatenbough |
| 6,470,696 B1 | 10/2002 | Palfy et al. |
| 6,704,944 B2 | 3/2004 | Kawainshi et al. |
| 6,896,366 B2 | 5/2005 | Rice et al. |
| 6,927,368 B2 | 8/2005 | Cao et al. |
| 7,387,022 B1 | 6/2008 | Korniyenko et al. |
| 7,648,234 B2 | 1/2010 | Welchel et al. |
| 8,399,805 B2 | 3/2013 | Biddell |
| 2003/0091089 A1 | 5/2003 | Krausse |
| 2004/0050072 A1 | 3/2004 | Palfy et al. |
| 2004/0050076 A1 | 3/2004 | Palfy et al. |
| 2006/0289458 A1 | 12/2006 | Kim et al. |
| 2008/0290081 A1 | 11/2008 | Biddell |
| 2013/0043233 A1 | 2/2013 | Elser et al. |

* cited by examiner

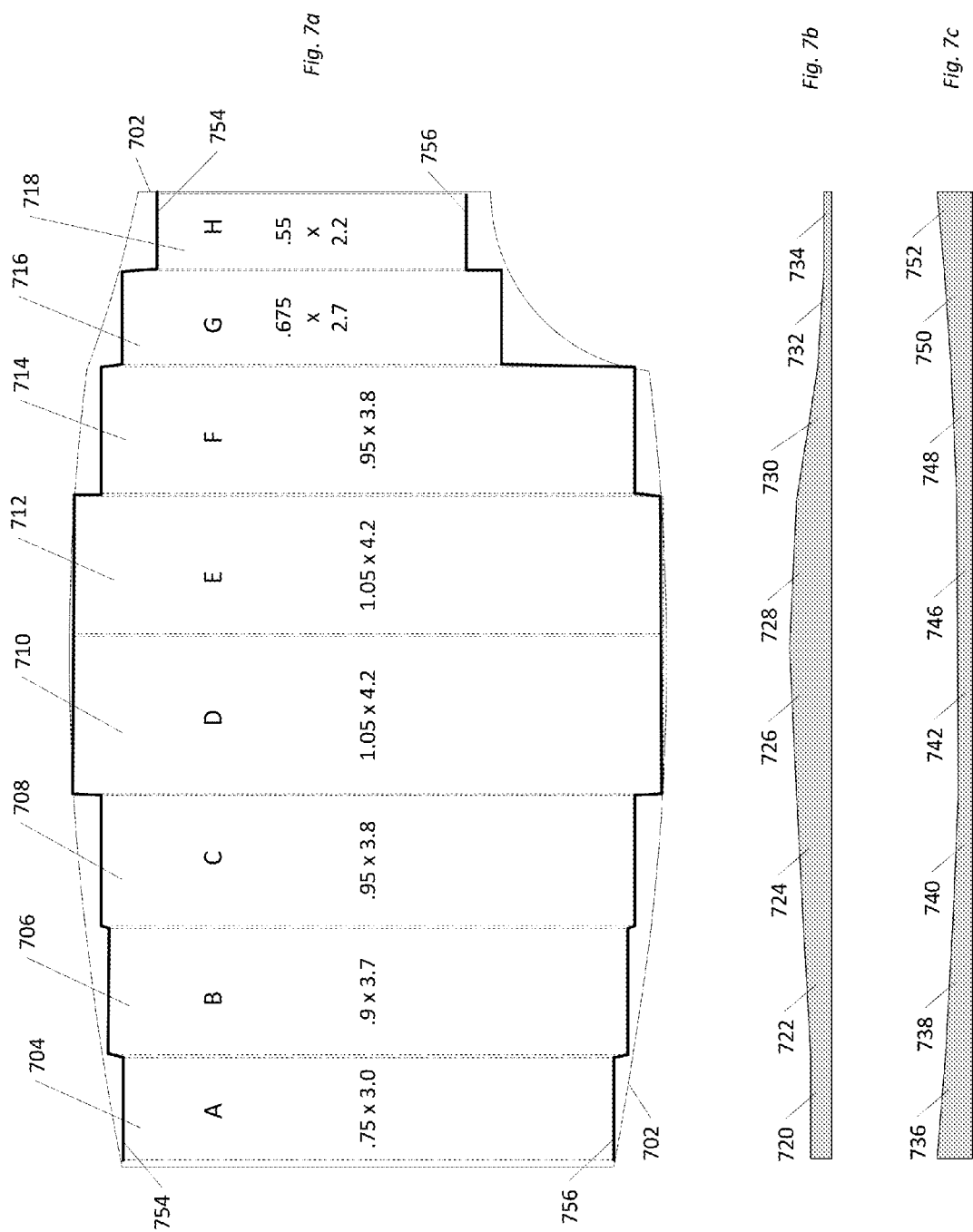

| Heating Element Resistance | PWM Adjustment Factor |
|---|---|
| 8.0 | 0.80 |
| 8.2 | 0.82 |
| 8.4 | 0.84 |
| 8.6 | 0.86 |
| 8.8 | 0.88 |
| 9.0 | 0.90 |
| 9.2 | 0.92 |
| 9.4 | 0.94 |
| 9.6 | 0.96 |
| 9.8 | 0.98 |
| 10.0 | 1.00 |
| 10.2 | 1.02 |
| 10.4 | 1.04 |
| 10.6 | 1.06 |
| 10.8 | 1.08 |
| 11.0 | 1.10 |
| 11.2 | 1.12 |
| 11.4 | 1.14 |
| 11.6 | 1.16 |
| 11.8 | 1.18 |
| 12.0 | 1.20 |

FIG. 10

MICRO-CURRENT SENSING AUTO-ADJUSTING HEATER SYSTEM FOR EYE-SHIELD

CROSS-REFERENCE TO AND INCORPORATION BY REFERENCE OF RELATED APPLICATION

This application is a continuation-in-part of prior co-pending U.S. patent application Ser. No. 14/040,683, to Cornelius, for Multiregion Heated Eye-shield, filed 29 Sep. 2013, Publication No. US-2014-0027436-A1 (hereafter also referred to as the "Parent Application"), which is a continuation-in-part of U.S. patent application Ser. No. 13/397,691, to Cornelius, for PWM Heating System for Eye-shield, filed 16 Feb. 2012, which issued as U.S. Pat. No. 8,566,962, issued 29 Oct. 2013 (hereafter also referred to as "the PWM Application"). This application claims the benefit and the priority of the Parent Application and the PWM Application. The Parent Application and the PWM Application are hereby incorporated by reference in this application.

FIELD OF INVENTION

This invention relates to heating systems employing resistive heating elements on eye-shields, and more particularly to improved heating systems for portable anti-fog eye-shields able to be worn on users' heads, to enable consistency in heating from one portion of an eye-shield to another portion of the eye-shield and/or to enable consistent heating from one eye-shield to the next eye-shield.

BACKGROUND OF THE INVENTION

It is often desirable to use sport goggles, dive masks and other highly portable transparent eye-protecting shields in environments involving conditions which contribute to condensation build-up on the eye-shield and where even momentary impairment of vision by fogging would be problematic. When the temperature of such an eye-shield has dropped below a dew-point temperature, i.e., the atmospheric temperature below which water droplets begin to condense and dew can form, fogging has occurred and has obstructed vision.

A common characteristic of such portable eye-protecting shields is the fact that they are lightweight enough to be worn on a user's head and are positioned relatively closely to a user's face such that the user's breath and body heat exacerbates fogging conditions. Examples of fog-prone sport goggles intended for use during winter activities have included goggles for downhill skiing, cross-country skiing, snowboarding, snowmobiling, sledding, tubing, ice climbing and the like, and are widely known and widely utilized by sports enthusiasts and others whose duties or activities require them to be outside in snowy and other inclement cold-weather conditions. Examples of fog-prone goggles and eye-shields used in military or tactical environments, including cold weather and other environments, have included ballistics grade goggles used in military or hunting operations, goggles for use in correctional facilities, protective eyewear and goggles for use in police work, crowd control, riot control, or swat operations. Examples of fog-prone dive masks have included eye and nose masks independent of a breathing apparatus, as well as full-face masks in which the breathing apparatus is integrated into the mask. Examples of fog-prone eye-protecting shields have included a face shield that a doctor or dentist would wear to prevent pathogens from getting into the user's mouth or eyes, or a transparent face shield portion of a motorcycle or snow-mobile helmet. Fogging that impairs vision is a common problem with such goggles, dive masks and eye-protecting shields.

There have been various conductive apparatus devised for preventing condensation build-up on eye-shields for eye-protecting shields. The purpose of such prior conductive apparatus has been to provide eye-shields that may be maintained free of condensation so that users would be able to enjoy unobstructed vision during viewing activities. However, without apportionment of the heater on the irregularly-shaped eye-shield lenses of these apparatus, such eye-shields have been subject to problems of creating hot spots on the irregularly-shaped lenses and have not provided for customizable heating of the lenses.

Thus, there have been developed a newer system as disclosed in co-pending U.S. patent application Ser. No. 14/040,683, to Cornelius, for Multiregion Heated Eye-shield, filed 29 Sep. 2013, Publication No. US-2014-0027436-A1 (hereafter also referred to as the "Parent Application"), which is a continuation-in-part of U.S. patent application Ser. No. 13/397,691, to Cornelius, for PWM Heating System for Eye-shield, filed 16 Feb. 2012, which issued as U.S. Pat. No. 8,566,962, issued 29 Oct. 2013 (hereafter also referred to as "the PWM Application"). This newer system has made use of apportioned heaters on an eye-shield, but there has developed the potential problem that the resistivity of the heater from one portion of the heater to another portion of the heater on the eye-shield may be different, and this would also lead to variations in heating across the eye-shield. Further, an additional problem associated with a thin-film heater for eye-protecting shields has been the variations of resistance in the heaters encountered from one eye-shield to another eye-shield.

Before the Parent Application and the PWM Application, no prior eye-shield condensation prevention system had taught a system for employing an apportioned thin-film heating system for evenly heating an irregularly-shaped eye-shield, or alternatively for customized heating of such an eye-shield according to a lens heating profile. Accordingly, the undesirable effects on even, uniform, or otherwise expected, heating, resulting from varied resistance of a thin-film heater across an eye-shield, or from one eye-shield to the next, had not been appreciated until the Parent Application and the PWM Application had been implemented.

The defogging ability of a thin-film heater on an eye-shield is determined by the amount of power supplied to the thin-film heater, the time the power is supplied, and the electrical resistance of the thin-film heater. Thus, variations in resistance of such thin-film heaters have resulted in variations of heating temperatures resulting on the eye-shields, or eye-shield regions, themselves. These variations of resistance have resulted primarily from difficulties experienced in applying the thin-film heating elements uniformly across the eye-shield surfaces, and from difficulties experienced in applying the thin-film heating elements consistently uniformly from one eye-shield to another. Also, different methods applying thin-film heating elements to eye-shields may lead to difference resistance values obtained. Thus, the uneven and inconsistent application of thin film heating elements has created variations in resistivity across the eye-shield regions, and as a result, variations in heat supplied by the thin-film heaters on the respective eye-shield regions.

Such variations in thin-film heater thickness could result, for example, when a thin-film heater has been applied from a single source that is variable in thickness from one region of the source to another region of the same source (e.g., a single roll of PET with an uneven thin-film of Indium-Tin-Oxide (ITO) thereon due to uneven application by sputtering), or perhaps when each region comes from a different source of thin-film heater material (e.g., from two different rolls of PET with varying thickness thin-film heaters on one roll relative to the other roll). Either way, the problem is the same which has led to uneven, or otherwise undesirable, heating characteristics. Accordingly, there have been variations of resistance encountered from one region of an eye-shield to another region of the same eye-shield, or from one eye-shield to another eye-shield in a group, or batch, of eye-shields.

Prior goggles and eye-shields with electronic systems have been primarily used in environments requiring a high degree of portability, that is, where a power source for powering the electronics for the device has been advantageously carried on a strap for the goggle or on the goggle itself, as shown and described in co-pending U.S. patent application Ser. No. 13/519,150, by McCulloch et al., for Goggle with Easily Interchangeable Lens that is Adaptable for Heating to Prevent Fogging.

Some examples of disclosures providing for heating of goggle lenses include the following: U.S. Pat. No. 4,868,929, to Curcio, for Electrically Heated Ski Goggles, comprising an eye-shield with embedded resistive wires operatively connected via a switching device to an external power source pack adapted to produce heating of the eye-shield for anti-fog purposes. The Curcio disclosure does not teach even heating of a lens, or alternatively customized heating of a lens, by employing a certain configuration of thin-film heating material on the lens. Accordingly, Curcio likewise does not teach even and consistent heating of multiple regions of a single lens. Nor does Curcio teach even and consistent heating of one eye-shield to the next eye-shield of a plurality of eye-shields.

US Patent Application No. 2009/0151057A1 to Lebel et al., for Reversible Strap-Mounting Clips for Goggles, and U.S. Pat. No. 7,648,234 to Welchel et al., for Eyewear with Heating Elements, disclose use of thin-film heating elements used for heating an eye-shield with a push-button switch for turning on power from a battery carried on an eyewear band or eyewear arm. Neither Lebel et al. nor Welchel et al. teach even heating of an irregular-shaped lens, or alternatively customized heating of the lens, by employing a certain configuration of apportioned thin-film heating material on the lens. Accordingly, neither Lebel nor Welchel et al. teach even and consistent heating of multiple regions of a single eye-shield or consistent heating of one eye-shield to the next eye-shield of a plurality of eye-shields.

U.S. Pat. No. 5,351,339 to Reuber et al., for Double Lens Electric Shield, recognizes the problem of un-even heating where an electro-conductive film is deposited on an irregular-shaped visor lens and proposes a specific bus bar configuration (electrodes 50 and 60) that addresses the problem of making the distance between electrodes substantially the same for fairly uniform flow of electrical current across the electro-conductive film. However, Reuber et al. does not disclose even heating of a lens, or alternatively customized heating of the lens in accordance with a heating profile, by employing a certain configuration of apportioned thin-filmed heating material on the lens. Further, the eye-shield of Reuber et al. was more uniform than that of a conventional goggle having a cutout portion adapted to fit over the bridge of a user's nose. Accordingly, the configuration of the electrode bus bars of Reuber et al. would not suffice for a more conventional goggle lens configuration. Still further, Reuber does not teach even and consistent heating of one region of an eye-shield to the next region of the same eye-shield, or consistent heating among multiple eye-shields, through the use of an apportioned thin-film heater.

Thus, variations in the thickness of thin-film heaters applied to heat eye-shields to prevent fogging have led to uneven heating over the entire surface of an irregular-shaped eye-shield, and in particular over multiple regions of a single irregular-shaped eye-shield or multiple irregular-shaped eye-shields. Goggles and dive masks, and their eye-shields, are manufactured with an irregular shape required to maintain a position close to the face of the wearer and allowing cutouts for the nose and extended edges for peripheral vision. While various general attempts to evenly heat an eye-shield across its entire surface have been made with serpentine wires included on, or within, eye-shield lenses, as for example in published US Patent Application No. 2008/0290081A1 to Biddel for Anti-Fogging Device and Anti-Fogging Viewing Member, and U.S. Pat. No. 4,638,728 to Elenewski for Visor Defroster, even heating of an irregular-shaped eye-shield, or customized heating of such an eye-shield, with an apportioned thin-film heater, has not been taught in the prior art. Similarly, the prior art has not disclosed even and consistent heating of one region of an eye-shield relative to another region of the same eye-shield, or consistent heating from one eye-shield to the next, despite variable thicknesses of thin-film elements used.

The goggle of Lebel et al. would be susceptible to hot spots, and therefore using such a device in a limited battery-powered application would have unduly discharged the battery. The reason for the hot spots has been because the electrical resistivity between the electrical connections across the resistive elements on the eye-shield has been greater or lesser at different locations on the eye-shield such that the amount of electrical current consumed in the areas with less distance between terminal connections is greater and the amount of electrical current consumed in areas with greater distance between the terminal connections is less. For example, where the terminals are on either side of the lens in a resistive wiring application, there have been problems with evenly heating the lens since the distance the wire has had to travel from one terminal to the other has been greater for those wires traveling over the bridge of the nose and down under the eyes than other wires that travel the shorter distance across a central portion of the lens. To overcome fogging conditions enough power must be applied to overcome the fog in the areas with the greatest distance between the terminal connection points, causing the shorter distance areas to overheat, which in turn has wasted power. Thus, the problem has resulted in limited usefulness of heating of goggle eye-shields. Because of the irregular shape of eye-shields, these problems have existed whether one has considered resistive-wire applications or resistive-film applications.

Still another problem associated particularly with goggles and dive masks is the amount of space provided between the eye-shield portion of the device and the user's face. Where insufficient space has been provided, the wearing of corrective lens eye glasses within the goggle or mask has been prohibited. Further, where excess distance has been provided between the shield portion of the device and the user's eyes, the ability to incorporate corrective lenses into the goggle or mask eye-shield itself has been prohibited. Increased distance between the user's eyes and the eye-shield has improved anti-fogging capability in typical air-flow dependent anti-fog goggles, however, locating the eye-shield at such a great distance from the user's eyes to facilitate anti-fogging has made corrective goggle lenses ineffective for correcting vision, because excessive lens thickness would have been required to accommodate the higher degree of curvature necessary in the lens to make the necessary vision correction. Thus, what has been long needed in the corrective lens goggle, or dive mask, art is a technology that would both permit a corrective eye-shield lens to be sufficiently close to the user's eyes to function properly from a vision correction perspective, but which is also capable of effective fog prevention. Thus, there has developed a need to balance regions of eye-shields to enable even heating of eye-shields across the entire eye-shield surface without excessive use of power or hot spots and without excessive space between the user's eyes and the eye-shield itself for vision correction lens purposes.

SUMMARY OF THE INVENTION

The multiple-region eye-shield of the present invention provides a thin-film conductive heating element on the eye-shield or lens surface that is divided into multiple regions, for example regions according to irregular and differently-shaped portions of the lens such as directly over the bridge of the nose as compared to directly in front of the eyes, to enable even, or alternatively custom, heating of such differently-shaped or sized regions.

In accordance with an aspect of the invention, there is provided an eye-shield adapted for use with a powered circuit having a given voltage, for preventing fogging of the eye-shield and for preventing hot spots on the eye-shield. The eye-shield in accordance with this aspect of the invention comprises: An optically-transparent substrate adapted for protecting at least one of a user's eyes and adapted for defining at least a partially-enclosed space between at least one of the user's eye's and the substrate; and a plurality of electrically conductive regions of optically-transparent, electrically-resistive thin-film conductive heating material on the substrate. Preferably, in accordance with this aspect of the invention, an eye-shield capable of substantially even heating across the entire eye-shield is provided, even if the eye-shield is an irregularly-shaped eye-shield.

Preferably, in accordance with this aspect of the invention, the number of conductive regions and the size of each conductive region is determined in accordance with predetermined power densities for the regions of an irregularly-shaped lens. In accordance with one embodiment of this aspect of the invention, the power density of each region is preferably the same as the power density of each other region. In accordance with another embodiment of this aspect of the invention, the power density of at least one region would be different than the power density of another region.

The number of the plurality of regions and the size of each region on the substrate may, or may not, be made in accordance with a heating profile. In this regard, a heating profile could be simply an understanding on the part of the designer of the lens that he or she would like even heating, to the degree feasible, across the lens substrate as in accordance with this aspect of the invention. Or, in accordance with another aspect of the invention, an understanding, or profile, may involve custom heating of an eye-shield, as for example may be the case for a snowboarder as compared to a skier. A heating profile may typically be used where one or more parts of the eye-shield are to be intentionally made warmer than other parts of the eye-shield (e.g., where one side is warmer than another, or the edges are warmer than the middle of the eye-shield). Thus, for example, in the case of a snowboarder, one side of the lens corresponding to the forward foot of the snowboarder may require more heat since the snowboarder typically stands more sideways while going down a hill. In accordance with either the even heating aspect of the invention, or the custom heating aspect of the invention, a heating profile may include a more detailed written profile including one or more of defined lens heating material regions, identification of size and shape of lens heating material regions, desired regions of relative increased heating, or decreased heating, and identification or calculation of respective region power densities. Thus, the heating profile may be very simple, even just understood, or more complex and even written, and determines whether balanced, or even, heating is desired from one conductive region to the next across the eye-shield, or whether a custom profile of full or proportional heating for each of the regions would be more desirable for a given eye-shield configuration or purpose. The invention may be used to produce both regular and more irregular-shaped eye-shields that are evenly heated, or alternatively in accordance with a custom heating profile.

In one embodiment of the invention, each conductive region is isolated by an electrically conductive area on the eye-shield substrate. This embodiment of the invention enables a designer and manufacturer to provide for the driving of separate areas of the eye-shield with separate electronics channels such as that described in the co-pending U.S. patent application Ser. No. 13/397,691, Publication No: US2013/0212765A1, to Cornelius (the "PWM Application").

In another embodiment of the invention, each conductive region is provided as being contiguous with adjacent regions of heating material on the eye-shield. This embodiment of the invention enables a designer and manufacturer to produce eye-shields that either heat evenly, or heat according to a profile, with or without a PWM control, and thus this embodiment of the invention simplifies the manufacturing of a goggle, thus allowing for a less costly goggle.

In connection with either embodiment of the invention described above, the eye-shield in accordance with this aspect of the invention may further comprise at least two bus bars connected to the conductive regions and adapted for interconnecting the conductive regions with the powered circuit. This embodiment of the invention allows a designer and manufacturer of eye-shields to work with a single channel circuit provided in a goggle. Alternatively, in either embodiment of the invention, the eye-shield in accordance with this aspect of the invention may further comprise a plurality of conductive bus-bars connected to each of said conductive regions and adapted for interconnecting each said conductive region with the powered circuit. This embodiment of the invention allows a designer and manufacturer of heated eye-shields to work with a multichannel circuit to provide even greater control over heating of the eye-shield.

In accordance with either aspect of the invention, and with any of the embodiments of the invention, the specified resistivity of the heating material may be either varied in accordance with varying formulations of heating material, for example 10-ohm per square ITO (or other heating material), 20-ohm per square ITO, etc., or the thickness of the heating material may be varied to vary this resistivity. Or, alternatively, some combination of varied formulation and varied thickness of heating material may be employed in accordance with either aspect of the invention. Thus, in accordance with either aspect of invention and any of the embodiments of the invention, the heating material of at least one of the plurality of conductive regions of the eye-shield may be provided to have a specified resistivity per square that is different from the specified resistivity per square of the heating material of another of the plurality of conductive regions of the eye-shield. Further, the formulation of the heating material of at least one of the plurality of conductive regions may be selected in accordance with a given resistivity per square for the heating material. Still further, the resistivity per square of the heating material of at least one of the plurality of conductive regions may be determined at least in part by varying the thickness of application of the heating material to the substrate. In this way, the designer and manufacturer of eye-shields is enabled greater flexibility to design the eye-shield and its desired heating characteristics, whether with or without a heating profile, by selecting from available materials and thicknesses in accordance with either aspect or any embodiment of the invention. Such flexibility of design options for the eye-shield during design and manufacture makes balancing of power densities across the plurality of conductive regions easier to accomplish given size, shape, voltage input and power density requirements.

Also, regarding the eye-shield having a customized heating aspect and/or embodiment of the invention (whether in an electrically-isolated heating regions embodiment or a contiguous heating regions embodiment), it will be apparent from the foregoing that there may be provided at least one region of the plurality of conductive regions having a power density that is different than the power density of another of the plurality of conductive regions. Thus, custom heating profiles may be more easily enabled by employing one, or more, conductive regions of different resistivity per square than another, or others, or differing thicknesses of conductive regions, or heating elements, on the same eye-shield, to accommodate particular needs, such as extreme condition performance requirements, custom applications, highly irregular-shaped eye-shields, and the like.

In accordance with another aspect of the invention, for all embodiments of the invention and whether an even heating or a custom heating profile is used, the substrate of the eye-shield is preferably of an irregular shape, since it is such eye-shields that would otherwise be prone to uneven heating. In this context, the term irregular shaped eye-shield, or substrate, means an eye-shield or substrate of any shape other than square or rectangular.

Thus, in accordance with an aspect of the invention, there is provided an eye-shield adapted for use with a powered circuit having a given voltage, for preventing fogging of the eye-shield and for preventing hot spots on the eye-shield, comprising: An optically-transparent substrate adapted for protecting a user's eyes and adapted for defining at least a partially-enclosed space between the user's eyes and said substrate; and a plurality of electrically-isolated conductive regions of optically-transparent electrically-resistive thin-film conductive heating material on the substrate, wherein the power density of each region is the same as the power density of each other region and wherein the heating material of at least one of the plurality of conductive regions has a specified resistivity per square that is different from the specified resistivity per square of the heating material of another of the plurality of conductive regions.

Or, alternatively, in accordance with an alternative embodiment of an aspect of the invention, there is provided an eye-shield adapted for use with a powered circuit having a given voltage, for preventing fogging of the eye-shield and for preventing hot spots on the eye-shield, comprising: an optically-transparent substrate adapted for protecting a user's eyes and adapted for defining at least a partially-enclosed space between the user's eyes and the substrate; and a plurality of contiguous conductive regions of optically-transparent electrically-resistive thin-film conductive heating material on the substrate, wherein the power density of each region is the same as the power density of each other region and wherein the heating material of at least one of the plurality of conductive regions has a specified resistivity per square that is different from the specified resistivity per square of the heating material of another of the plurality of conductive regions.

Further, it will be appreciated from the foregoing that the resistivity per square of the heating material of the at least one of the plurality of conductive regions may also be determined, at least in part, by varying the thickness of application of the heating material to the substrate. Accordingly, it will be appreciated that the resistivity of any region of heating material as part of the invention may be varied either or both by choosing a heating material having a different formulation and by varying the thickness of the application of the heating material to the lens substrate.

An eye-shield in accordance with an aspect of the invention provides a unique fog-prevention eye-shield for use in connection with ski goggles, dive masks, motorcycle helmet visors or snowmobile helmet visors, and the like. Further an eye-shield in accordance with an aspect of the invention provides a unique fog-prevention eye-shield for use in medical, high-tech, testing or other working environments where fogging of a visor or eye-shield may become a problem. The elimination of undesirable hot spots on the eye-shield is accomplished with an aspect of the invention in that each region may be designed to an appropriate size and shape that yields a power density that is appropriate for the size of the region being heated. And while a device in accordance with an aspect of the invention enables prevention of fogging while also preventing hot spots on the eye-shield without the need for a pulse-width modulated (PWM) system as described in the PWM Application, the device also may be used in connection with such a PWM system if so desired for other reasons. Thus, an eye-shield device in accordance with at least one aspect of the invention accomplishes heating of the eye-shield, and thus prevention of fogging while also preventing hot spots on the eye-shield in that the balancing of the heating of the eye-shield, or conversely customized zone heating of the eye-shield, is determined by the eye-shield itself and at the time of design and manufacture. This makes provision of the eye-shield, and the resulting goggle, mask or other eye-shield, more cost effective to produce and more functionally efficient in preventing fogging and hot spots on the eye-shield, since less complicated and less expensive electronics are able to be used to produce the eye-shield and hence the resulting eye wear.

The foregoing aspects of the invention provide an eye-shield that is adapted for being heated in an electrical circuit to raise the temperature of preferably an inner surface of the eye-shield above the dew point in order to prevent fogging, without creating undesirable hot spots in portions of the eye-shield, e.g., over the bridge of the nose, where a unitary evenly-applied heating material would produce too much power for the region causing it to overheat. Further, with the use of PWM to maximize efficiency of the system as disclosed in the PWM Application, the foregoing benefits and properties are able to be accomplished by powering the eye-shield with a single, highly-portable power source, such as a lithium-ion battery retained in the frame or strap of the goggle. However, with the aid of one or more aspects of the present invention, a simple circuit consisting of one or more batteries, such as lithium-ion batteries, and an on/off switch, would be sufficient to provide a fog-free goggle lens that is either evenly heated across the entire lens, or alternatively, is heated according to a customized pattern.

The device of an aspect of the invention enables balanced, or alternatively customized, heating of the eye-shield with, or without, a pulse-width modulated (PWM) heater driver as described in the PWM Application. Thus, a device in accordance with an aspect of the invention provides an eye-shield that is easy and cost effective to produce, and the eye-shield will also function to allow even or customized heating with a variety of different heated goggles, masks or visors. While a PWM heater driver like that disclosed in the PWM Application would allow variability of the output of the heating material on the eye-shield and would allow even greater efficiency of the system in terms of battery usage, a PWM heater driver is not necessary for achievement of certain aspects of the invention, since if a user simply desires an even or customized heating profile of the eye-shield, without the ability to vary the heat output of the eye-shield as possible to conserve energy with a single-PWM channel heater driver, the user may simply use a constant voltage, constant output, heating system for the eye-shield of the invention to achieve the desired result. Thus, the invention may be adapted for use in connection with an eye-shield heating system utilizing a portable battery, as in the case of smaller batteries carried on a goggle body or strap, or also if a larger battery is available, as in the case of a battery on a snowmobile, airplane, automobile or other vehicle.

With any embodiment of any aspect of the invention, there may be applied a nonconductive protective coating over the heating material to protect the heating material. This protective coating secured to the heating material and the substrate helps ensure that the heating material will not be damaged, as with scratching, which could impair the functioning of the heating material on the eye-shield.

Any of the aspects of the method for making an eye-shield of the present invention, or the resulting eye-shield of the present invention, may be adapted for use in connection with the manufacture of a sport goggle or any protective eye-shield, such as for skiing, inner-tubing, tobogganing, ice-climbing, snow-mobile riding, cycling, running, working with patients, in other medical or testing environments, and the like. Further, any of the aspects of the invention may be adapted for use in the production of a diving mask eye-shield.

In accordance with another aspect of the invention, there is provided an eye-shield condensation prevention system which comprises an eye-shield adapted for protecting a user's eyes, the eye-shield having a surface area divisible into at least one region for facilitating region heating of the eye-shield to a desired temperature, a power source, at least one pulse-width modulator, at least one microcomputer, and at least one heating element. The at least one heating element is located on and corresponds with the at least one region, which will facilitate region heating of the eye-shield. The at least one heating element corresponds with the at least one pulse-width modulator. The eye-shield condensation preventing system in accordance with this aspect of the invention further comprises a sensing circuit, also known as a micro-sensing circuit, for comparing voltage sensed from the power source and heating element resistance voltage. The eye-shield condensation preventing system of this aspect of the invention further comprises at least one circuit that interconnects the power source, the at least one pulse-width modulator, the at least one microcomputer, the at least one corresponding heating element for heating the eye-shield and the sensing circuit. The at least one microcomputer relays information to the at least one pulse-width modulator that controls current. Controlling the current controls and maintains the temperature of the at least one heating element region to a temperature above an anticipated dew point of an operating environment, thus alleviating dew and condensation from the eye-shield. The microcomputer determines heating element resistance from the sensing circuit and adjusts the pulse-width modulator's control of current to the heater. Using the pulse-width modulator to control the current flowing to the heater of the eye-shield addresses the problem of variable heater resistances of thin-film heaters from one region of an eye-shield to another, or from one eye-shield to another, by compensating for variations in resistance that might otherwise be encountered from one of one eye-shield region to another eye-shield region and one eye-shield to another eye-shield. This aspect of the invention counteracts the effects of uneven application of thin-film heating elements, and varying resistances between different areas of an eye-shield and varying resistances from one eye-shield to another eye-shield.

In accordance with this aspect of the invention, the eye-shield condensation prevention system may comprise a plurality of pulse-width modulators corresponding to a plurality of eye-shield regions and a corresponding plurality of heating elements of a goggle lens. When corresponding a plurality of heating elements with a plurality of pulse-width modulators, the eye-shield condensation prevention system adjusts at least one of the pulse-width modulators' control of current to a corresponding eye-shield region and heating element. This adjustment of current compensates for variations in resistance on different areas of an eye-shield, or variations in resistance from one eye-shield to another eye-shield, as determined, for example, in testing of a batch of eye-shields.

Alternatively, in accordance with this aspect of the invention, the eye-shield condensation system further comprises a look-up table of heating element resistance values each associated with a corresponding plurality of pulse-width adjustment factors. This table facilitates calculations by the microcomputer for an appropriate adjustment to be applied to the at least one pulse-width modulator. This adjustment by the microcomputer compensates for variations in resistance encountered from at least one of one eye-shield region to another eye-shield region and one eye-shield to another eye-shield.

Still further, alternatively, in accordance with this aspect of the invention, there is provided a plurality of eye-shield condensation prevention systems, wherein a first of the eye-shield condensation prevention systems is used to enable pulse-width modulator duty cycle adjustments to maintain constant heat from at least one heating element of the first of the plurality of eye-shield condensation prevention systems relative to the at least one heating element of a second of the plurality of eye-shield condensation prevention systems, despite variations of heater resistance values from the first eye-shield condensation prevention system and the second eye-shield condensation prevention system. This aspect of the invention provides for consistent heating to be applied, despite variations in thickness of a thin-film heating element that is applied to the eye-shield, from one eye-shield region to another eye-shield region, and one eye-shield to another eye-shield. This aspect of the invention also addresses the issue of hot spots that occur on an eye-shield due to inconsistent thicknesses and resistances of a thin-film heating element, allowing for consistent heating across the entire surface of a goggle eye-shield by adjusting the overall amount of power that is supplied to an eye-shield. This allows for greater user control over the goggle eye-shield, letting the user set a temperature or setting that is consistent from one eye-shield to another eye-shield.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings wherein like reference characters refer to like elements.

BRIEF DESCRIPTION OF THE DRAWINGS

FIG. 7a is a graphic representation front view of another alternate embodiment of at least a portion of an eye-shield having a plurality of different-sized (in plan view), contiguous heating material regions on an irregular-shaped lens substrate and which may either have heating material regions of equal thickness or varied thickness;

FIG. 7b is a graphic representation bottom view of the alternate embodiment of the portion of heated eye-shield shown in FIG. 7a (assuming varied thickness heating element regions in FIG. 7a), wherein even heating across the plurality of contiguous heating element regions on the lens substrate is assumed and accomplished by applying different thicknesses of the same transparent thin-film conductive material to the lens substrate;

FIG. 7c is a graphic representation bottom view of the alternate embodiment of the portion of the heated eye-shield shown in FIG. 7a (assuming varied thickness heating element regions in FIG. 7a) wherein custom heating (i.e., cooler in the center and hotter at each end) across the plurality of contiguous heating element regions on the lens substrate is assumed and accomplished by applying different thicknesses of the same transparent thin-film conductive material to the lens substrate.

FIG. 10 is a two-dimensional look up table employed with a microcomputer (MCU) that creates a mapping of PWM adjustment factors to heating element resistance values.

DETAILED DESCRIPTION

Figure 1:
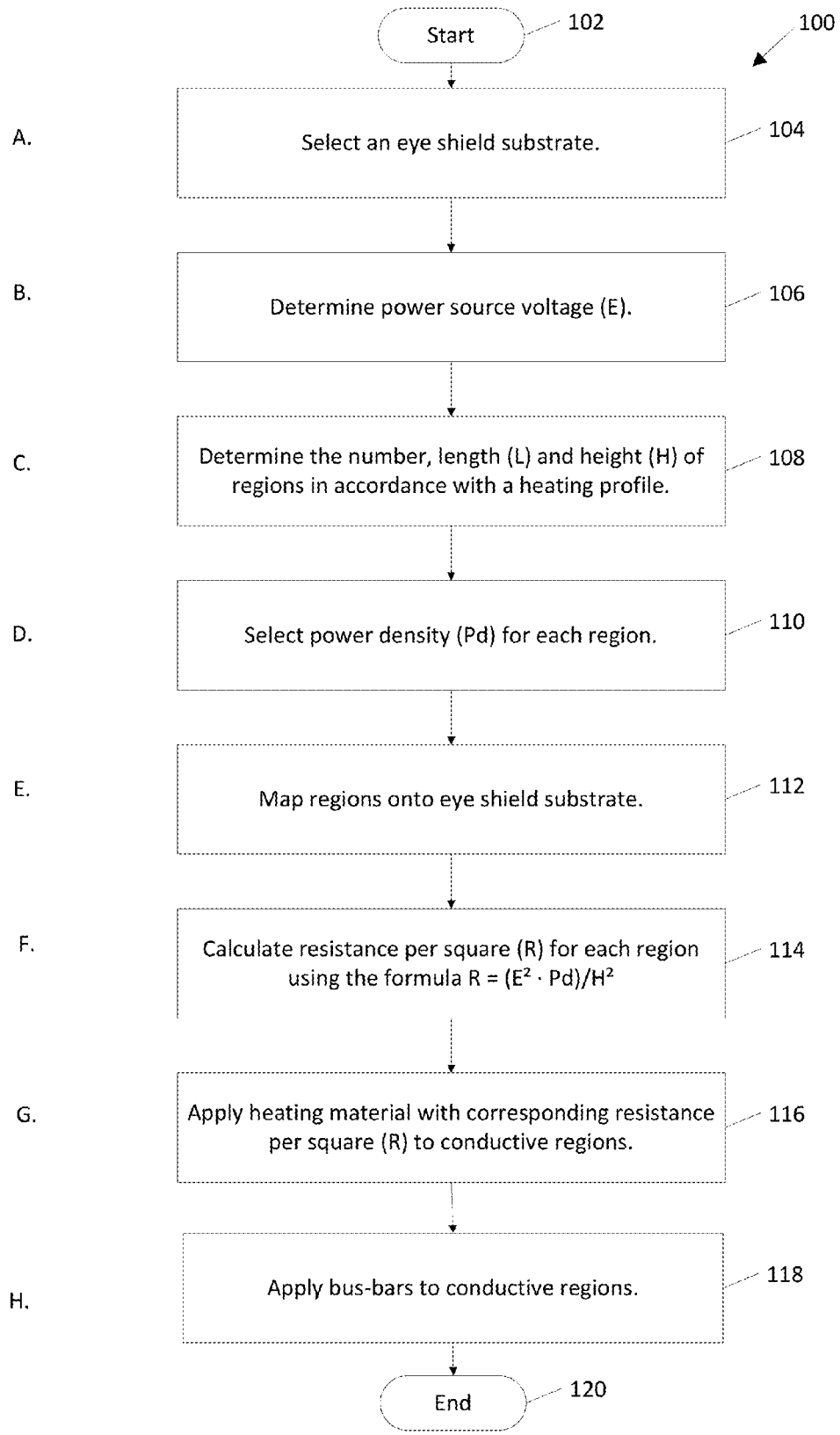
FIG. 1 is a flow chart regarding a method for adapting an eye-shield for use in a system for preventing fogging of the eye-shield while preventing hot spots on the eye-shield in accordance with an aspect of the present invention.

Referring to FIG. 1, a method 100 starting at origination location 102 for adapting an optically-transparent eye-shield for use in an electrical circuit to prevent fogging of the eye-shield while preventing hot spots on the eye-shield is disclosed. The method 100 comprises the following steps after starting at 102: selecting a nonconductive substrate at 104 defining an optically-transparent eye-shield and an outer periphery of the eye-shield; determining the power source voltage at 106, which is preferably a dc battery voltage source (e.g., 8.4 VDC which is the output of two 4.2 VDC, fully-charged, lithium-ion cells), but which may also be an output from a PWM driver; determining a heating profile, if any, for defining a heating pattern within the outer periphery of the eye-shield; determining at 108 the design, that is, the number of a plurality of regions and the size of each region (whether electrically-isolated or contiguous) in accordance with the heating profile; selecting at 110 a desired power density (Pd) for each region; mapping at 112 the heating regions onto corresponding regions of the eye-shield substrate; calculating the resistance per square (R) for each region using the formula $R=(E^2-Pd)/H^2$ where R=resistance per square, E=voltage, Pd=power density and H=the distance between the bus bars (expressed herein as H since it is the distance vertically, as in height, between upper and lower bus bars); applying 116 the heating material with corresponding resistance per square to corresponding conductive regions of the eye-shield to make each of the corresponding regions of the eye-shield adapted for conducting electricity; and applying at 118 bus-bars connected to the regions adapted for conducting electricity, the bus-bars and regions adapted for conducting electricity adapted to complete the electrical circuit powered by the battery. It will be appreciated that a plurality of upper bus bars and a single lower bus bar may be used, as shown and further described below in connection with FIG. 8, or a single upper bus bar and single lower bus bar may be used, as shown and further described below in connection with FIG. 5. It will be appreciated that there are several different ways of applying heating material, such as ITO, to a substrate, including commonly known methods of ion sputtering, coating, vacuum deposited coating, spraying, adhesive, adhesive backed and other methods.

An additional step of the process for creating a heated lens in accordance with present invention, may involve application of a nonconductive protective coating over the heating material to protect the heating material on the substrate. Thus, a protective coating is secured to the heating material and the substrate to help ensure that the heating material will not be damaged, as with scratching, which could impair the functioning of the heating material on the eye-shield substrate.

The eye-shield substrate (e.g., 212 of FIG. 2, 312 of FIG. 3, 602 of FIG. 6*a*, 702 of FIG. 7*a*, or 800 of FIG. 8) may be selected 104 from any of a number of materials, such as optically-transparent polycarbonate, other plastic, tempered glass, and the like, that are rigid enough to screen a user's eyes from such things as snowfall, rain, wind or other relatively small airborne particles in the user's environment. In the case of ski goggles, or other cold weather goggles, preferably the eye-shield substrate (e.g., 212 of FIG. 2, 312 of FIG. 3, 602 of FIG. 6*a*, 702 of FIG. 7*a*, or 800 of FIG. 8) is flexible enough to generally conform to the user's head and face with the eye-shield preferably being retained in a semi-flexible frame that holds the eye-shield around its periphery and also holds the eye-shield, via the use of a conventional strap, an appropriate distance from the user's face so as to form an enclosed space around and in front of the user's eyes, the frame typically providing a semi-permeable seal between the user's face and the rest of the goggle. Materials used for the various eye-shields employed with the present invention should also be resistant to shattering, cracking or otherwise breaking as necessary for the particular purpose for which they are chosen and as is known to those of ordinary skill in the art.

In the case of a dive mask, the eye-shield substrate (e.g., 212 of FIG. 2, 312 of FIG. 3, 602 of FIG. 6*a*, 702 of FIG. 7*a*, or 800 of FIG. 8) will typically be selected 104 from a somewhat more rigid plastic, or glass, material, and in the case of a visor or medical full face eye-shield the substrate would likewise be selected 104 of a somewhat more rigid plastic, or glass, material that is sufficiently light weight, but also sufficiently rigid to allow durable and repeated positioning of the eye-shield in place to protect the user's eyes. Selection 104 of the eye-shield substrate will preferably be of a material that is smooth to the touch, both on its inner (posterior) surface and its outer (anterior) surface and which is adapted to form a bond with the selected heating material. Eye-shield substrate materials are well known to those of ordinary skill in the art, and the selection of any type of optically-transparent eye-shield substrate shall fall within the scope of the claims appended hereto.

Referring still to FIG. 1, the number of the plurality of regions and the size of each region on the substrate may, or may not, be made in accordance with a heating profile. A heating profile could be simply a desire, thought or understanding on the part of the designer of the lens that even heating, to the degree feasible, across the lens substrate is desirable. Or, alternatively, a heating profile may involve custom heating of an eye-shield, as for example may be the case for a snowboarder as compared to a skier heating profile. Thus, a more formal heating profile may be used where one or more parts of the eye-shield are to be intentionally made warmer than other parts of the eye-shield (e.g., where one side is warmer than another, or the edges are warmer than the middle of the eye-shield), as opposed to simply even heating across the eye-shield. Thus, for example, in the case of a snowboarder, one side of the lens corresponding to the forward foot of the snowboarder may require more heat since the snowboarder typically stands more sideways while going down a hill. Whether even heating or custom heating is contemplated, a heating profile may include a more detailed written profile including one or more of defined lens heating material regions, identification of size and shape of lens heating material regions, desired regions of relative increased heating, or decreased heating, and identification or calculation of respective region power densities. Thus, the heating profile may be very simple, even just understood, or more complex and even written. A heating profile determines whether balanced, or even, heating is desired from one conductive region to the next across the eye-shield, or whether a custom profile of full or proportional heating for each of the regions would be more desirable for a given eye-shield configuration or purpose. The invention may be used to produce both regular and more irregular-shaped eye-shields that are evenly heated, or alternatively in accordance with a custom heating profile.

Referring now specifically to FIGS. 2-8, a progression, of less complex to more complex, of differing embodiments of the invention is shown to illustrate the many possible combinations of heating region sizes and shapes to accommodate differing sizes and shapes of substrates, differing methods of powering an eye-shield (e.g., dc battery and PWM), differing formulation and thicknesses of heating materials, differing applications (e.g., electrically-isolated and contiguous), and increasingly refined subdivisions of substrate to generalized heating or specific multichannel PWM systems. It will be appreciated that there will be other combinations of the foregoing basic elements to form a heated eye-shield lens which would not depart from the scope and spirit of the invention as set forth in the claims portion of this specification. For example, while the power source is shown in the present invention as coming from the top of the lens, with bus bars above and beneath the lens, it will be appreciated by those of ordinary skill in the art of electronics design that the power source may come from either side of the lens, or from the bottom of the lens, without departing from the true scope and spirit of the invention as claimed.

Figure 2:
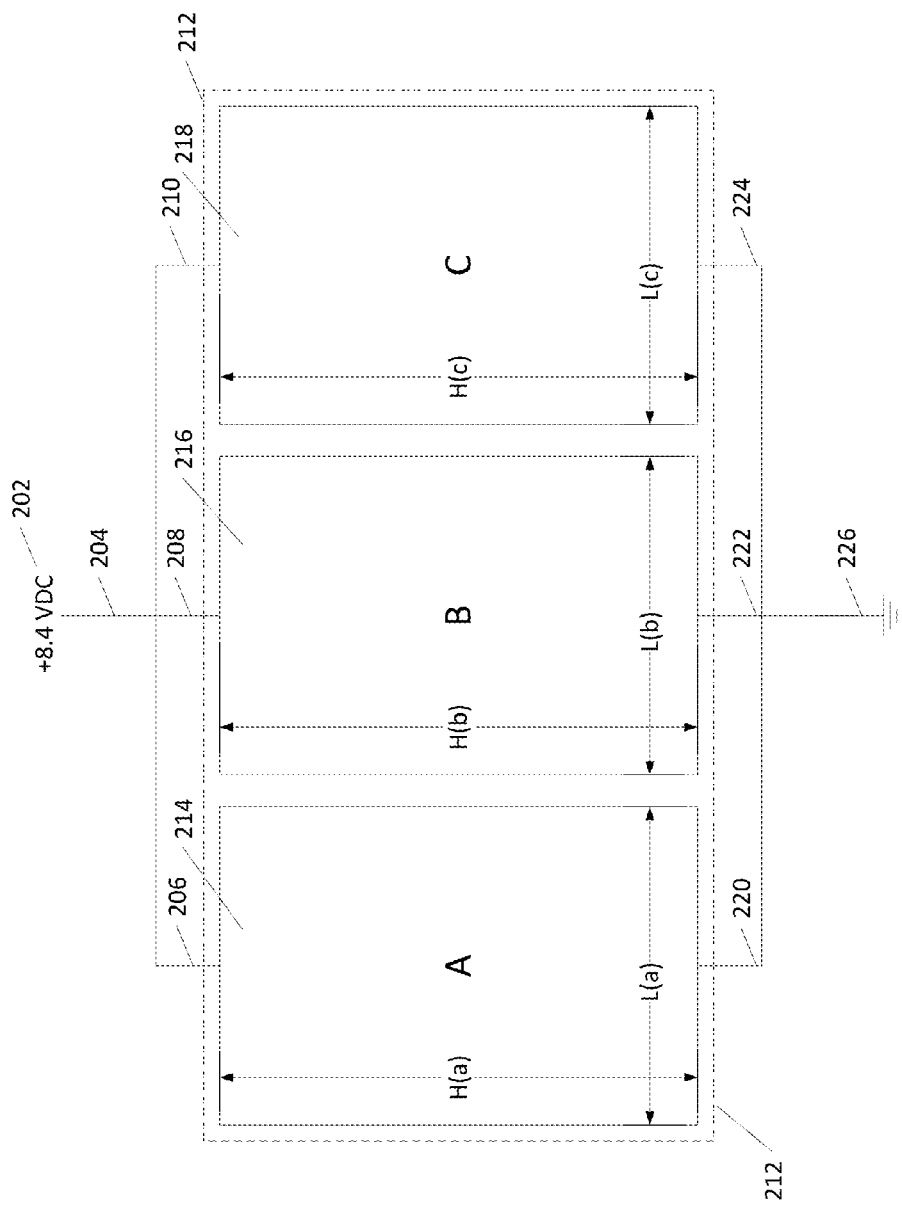
FIG. 2 is a graphic representation front view of at least a portion of an eye-shield having a plurality of equally-sized, electrically-isolated heating material regions on a regular-shaped lens substrate and connected in parallel with a dc battery.

Referring specifically to FIG. 2, there are shown three equally-sized, rectangular, electrically-isolated heating element regions A, B and C (214, 216, 218 respectively) on a regular (rectangular-shaped) eye-shield 212, powered from the top with an 8.4 volt direct current (VDC) voltage source 202 via parallel circuitry 204, 206, 208, 210 and grounded at 226 from the bottom via parallel circuitry 220, 222, 224. Each of these regions A, B and C have identical heating element coatings, such as formulated with the same resistivity (e.g., all may employ 20-ohm per square resistivity formulation of heating material) transparent and electrically conductive thin film heaters, such as ITO, zinc indium oxides (ZIO), zinc tin oxides (ZTO) or double-walled carbon nanotubes (DWNT). In FIG. 2, a simple version of an evenly-heated embodiment of the invention is shown wherein the power density (Pd) for these regions will be the same since each region is the same size, thickness and chemical formulation. Given a resistivity per square (R) of 20 ohms, we can calculate the power density of each region with the following formula:

$$Pd = E^2/R \cdot H^2,$$

where Pd is the power density, E is the voltage, R is resistance per square, and H is the height (distance between bus bars).

Adding values to this formula yields the following result: $8.4^2/20 \cdot 3^2 = 0.392$ watts per square=Pd. Again, this power density would be the same for each of the regions, and since all of the other foregoing factors would be equal (e.g., formulation of heating material, thickness of heating material and height of the heating material) the eye-shield 212 would be evenly heated across the entire eye-shield. Interestingly, by looking at the formula for power density, the distance L does not play a role, such that even if A, B and C were merged together into a single heating element, the power density would still be the same (assuming equal input voltage, equal H values, formulation of heating material, and thickness of heating material). Thus, in this simple case of a regular-shaped substrate, while a single heating element may be employed to achieve the same result, FIG. 2 illustrates that segmenting the heating element into multiple regions opens up the option of heating each region separately, as with separate batteries or with PWM channel controls per the Cornelius patent application Ser. No. 13/397,691, Publication No. US2013/0212765A1 (the "PWM Application"). Further, since even heating is not as difficult to achieve with thin-film heating elements on a rectangular or square substrate, FIG. 2 represents the simplest case for application of the invention of applying a plurality of heating elements to a single eye-shield substrate.

Further, no bus bars are shown in FIG. 2, illustrating the fact that, in accordance with the invention, the bus bars may either be on the eye-shield lens 212 itself, or housed in a goggle frame (not shown), depending upon the desired configuration of the eye wear.

Figure 3:
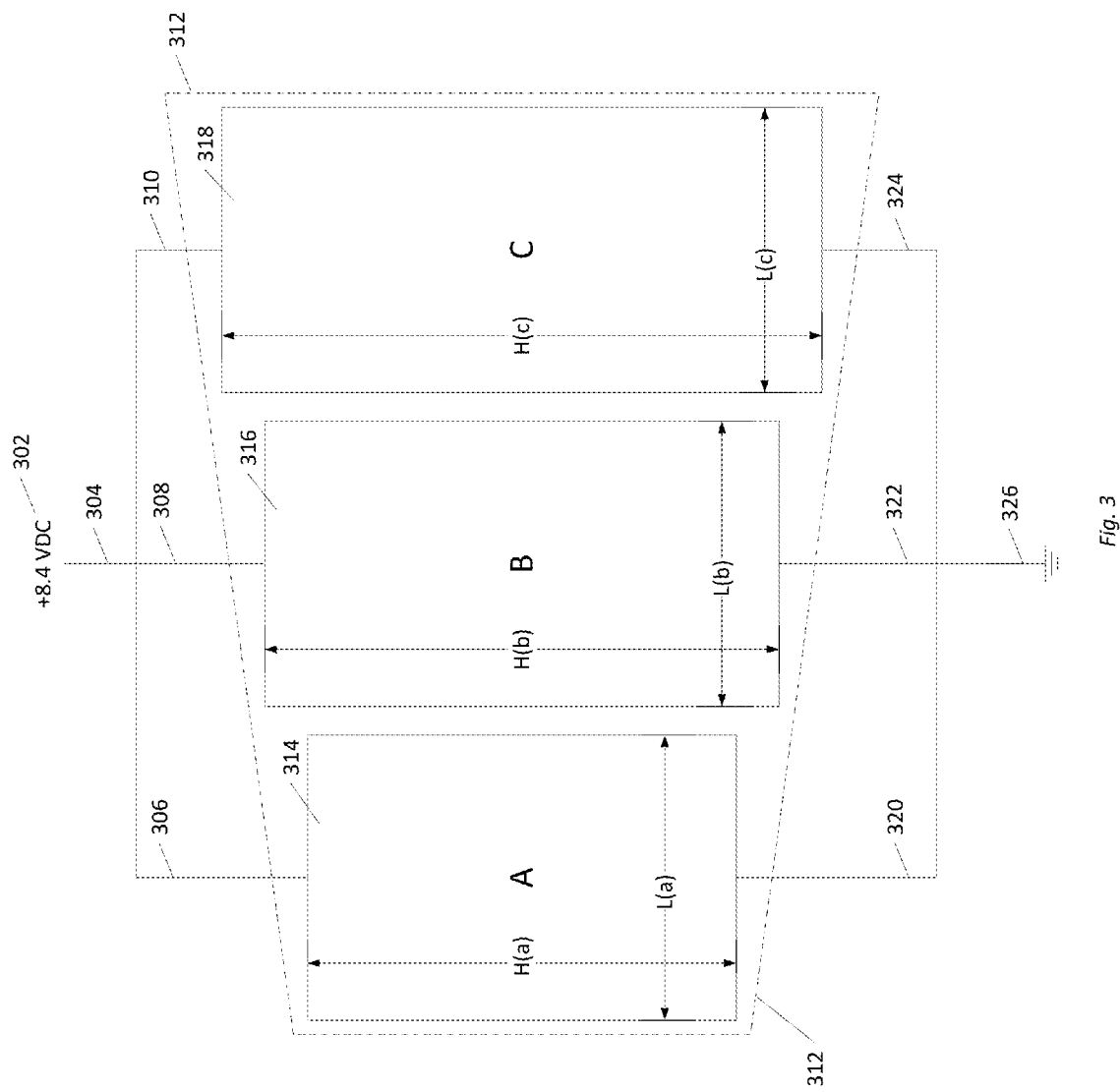
FIG. 3 is a graphic representation front view of an alternate embodiment of at least a portion of an eye-shield having a plurality of equal-length, electrically-isolated heating material regions on an irregular-shaped lens substrate and connected in parallel with a dc battery.

Referring now specifically to FIG. 3, there is introduced the added complexity over that shown in FIG. 2, of an irregularly-shaped substrate 312 requiring that the three electrically-isolated regions A, B, C (respectively 314, 316, 318) are not of equal height, but rather have been adjusted to fit the trapezoid-shaped substrate 312. Such an embodiment, without the invention, is of the type that would have begun to introduce uneven heating, because of an irregularly-shaped eye-shield substrate 312, into an eye-shield device. The embodiment of FIG. 3 illustrates that the higher the H value of the heating element material A, B, C (314, 316, 318), the lower the power density Pd. Thus, given a consistent resistivity per square (R) of 20 ohms, because of the different shapes A, B, C for covering the trapezoid-shaped substrate 312, the power density calculations yield different results as follows:

A: $Pd=E^2/R \cdot H^2$ adding values: $8.4^2/20 \cdot 3^2=0.392$ watts per square B: $Pd=E^2/R \cdot H^2$ adding values: $8.4^2/20 \cdot 3.6^2=0.272$ watts per square C: $Pd=E^2/R \cdot H^2$ adding values: $8.4^2/20 \cdot 4.2^2=0.200$ watts per square Thus, it can be seen that the shapes having a greater height (i.e., region C, 318), where other factors (input voltage, heating material thickness and resistivity formulation of heating material) are equal, have a lower power density (e.g., at 0.200 watts per square) than other shapes having a shorter height (H). The lower the power density of an area, the cooler that area will operate given same voltage input. Conversely, shapes having lesser height (i.e., shape A, 314), where other factors (such as input voltage, heating material thickness and resistivity of heating material) are equal, have a higher power density. Thus, since there has been a tendency for less high areas to become overheated, such as region A in this embodiment, segmenting the areas and designing a power density profile in accordance with a desired profile, whether even heating across the substrate, or custom heating, is advantageous because a designer and manufacturer of eye-shields may vary the formulation of heating material chosen, thickness of heating material applied, or height of a heating element in designing a lens according to desired parameters as shown and described later in connection with FIGS. 5-8.

It should be noted in connection with FIGS. 2-8, that the invention comprises a plurality of different embodiments of eye-shields ranging from simple to more complex. As an example of a more simple eye-shield in accordance with the invention, referring now to FIG. 3, each of the formulations of the areas A, B, C (314, 316, 318, respectively) is assumed to be of the same resistivity formulation material (20-ohms per square at 800 angstroms thick), the same thickness and the same voltage applied. Nevertheless, because of different heights (H) of the heating element regions, uneven heating of the regions of the embodiment of FIG. 3 would occur without application of the invention. As with any embodiment of the invention hereof, it will be appreciated that one may vary the formulation or the thickness of the heating element in order to alter its resistivity and thereby massage the power density of a region in accordance with a profile, whether it be even heating or custom heating.

Further, it should be noted in connection with FIG. 3 that while electrically-isolated segments or regions A, B, C (314, 316, 318) have been shown, these regions are driven by a single power source 302 via parallel circuit wires 306, 308, 310 and grounded at 326 via parallel circuit wires 320, 322, 324. A single bus bar is implied (or conversely multiple bus bars may be used to bring power to and from the shown single power source), thus making this embodiment of the invention suitable for controlled heating with or without PWM controlled heating. It should be noted that contiguous segments A, B, C could have also been employed with similar results in the case of a single power source 302 as shown.

Figure 4:
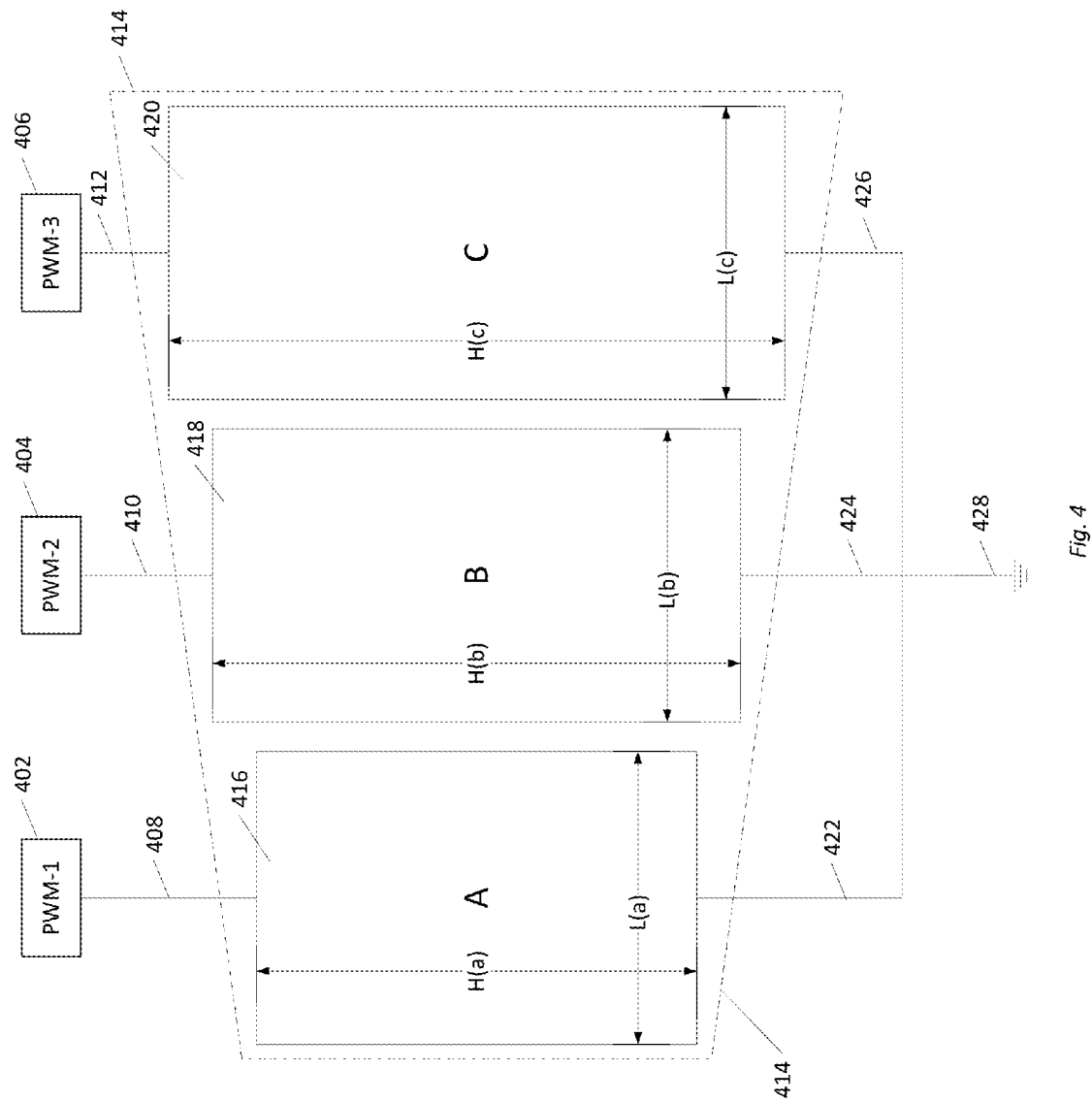
FIG. 4 is a graphic representation front view of the alternate embodiment of FIG. 3, but wherein the power to the eye-shield is controlled with a plurality of corresponding pulse-width modulated heater drivers.

Referring now specifically to FIG. 4, there is presented an embodiment of an eye-shield and substrate 414 that is similar to that of FIG. 3. However, in the embodiment shown in FIG. 4, there is specified a three-channel PWM circuit as shown in the PWM Application, comprising PWM-1 402, PWM-2 404, PWM-3 406 for driving the eye-shield through independent connections 408, 410, 412 for heating regions A, B, C (416, 418, 420, respectively). As with FIG. 3, each region A, B, C is of the same resistivity per square, e.g., 20 ohms per square, but in this embodiment, the amount of power to each region can be controlled by limiting the PWM output therefore delivering less power to B, and even less power to A, until both of those regions have the same power density (Pd) as that of C, to provide an evenly heated eye-shield. It should be noted that to achieve maximum balanced (even) power to all of the eye-shield regions A, B, C, the primarily available option is to limit the power (via PWM in this embodiment) to regions B and A, since those regions are going to otherwise run hotter than C (assuming that C is running at full power).

Figure 5:
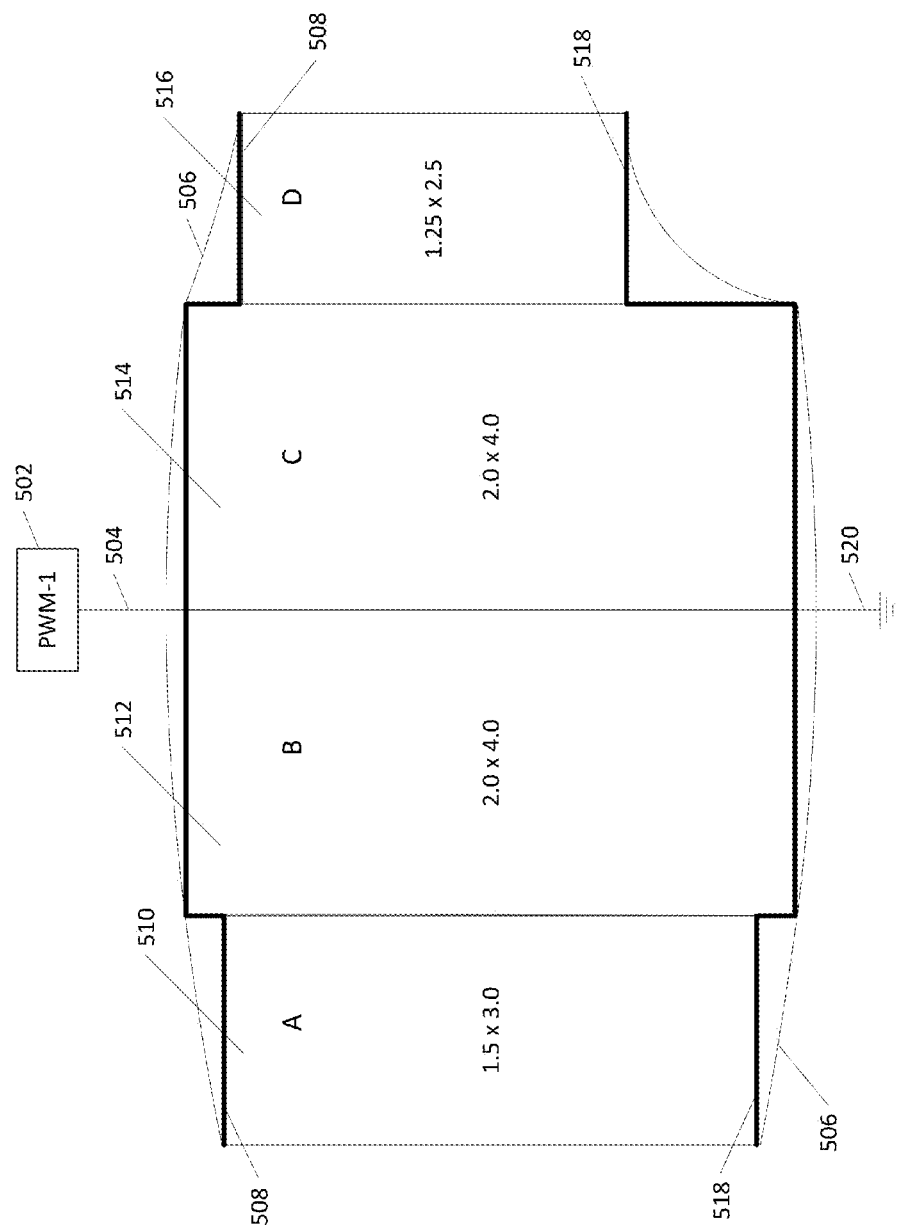
FIG. 5 is a graphic representation front view of another alternate embodiment of at least a portion of an eye-shield having a plurality of different-sized (in plan view), electrically-isolated heating material regions on an irregular-shaped lens substrate and connected in parallel with a dc battery via a single pulse width modulator using a single upper bus bar and a single lower bus bar.

Referring now to FIG. 5, there is shown an irregular-shaped substrate 506 for an eye-shield having four electrically-isolated heating element regions A, B, C, D (510, 512, 514, 516, respectively) thereon and powered by a single-channel PWM (PWM-1) power source 502 via circuit wires 504 to a single upper bus bar 508 and a lower bus bar 518 to ground wires 520. Using the formula $R=(E^2/Pd)/H^2$ the resistance value (R) of each region may be calculated, and according to the following assumptions, E=8.4 volts direct current (VDC), power density (Pd)=0.2 watts per square, and the given heights (distance between bus bars, e.g., Ha=3.0, Hb=4.0, Hc=4.0 and Hd=2.5):

A: $R=(E^2/Pd)/H^2$ adding values: $R=(8.4^2/0.2)/3^2=39.2$ ohms per square

B: $R=(E^2/Pd)/H^2$ adding values: $R=(8.4^2/0.2)/4^2=22.1$ ohms per square

C: $R=(E^2/Pd)/H^2$ adding values: $R=(8.4^2/0.2)/4^2=22.1$ ohms per square

D: $R=(E^2/Pd)/H^2$ adding values: $R=(8.4^2/0.2)/2.5^2=56.5$ ohms per square

Thus, by applying the heating material based upon these calculations, there has been produced an eye-shield having even heating (i.e., equal power densities) across the entire lens. This resistance per square outcome may be accomplished by selecting differing formulations of heating material for the different heating elements, or alternatively, this may be accomplished by applying heating material of equal resistivity formulation in differing thicknesses to the heating element regions in accordance with the calculations. Or, alternatively, there may be employed a combination of both methods of varying the resistivity. Finally, if custom heating is desired, this may be calculated and accomplished as further specified in connection with FIG. 6 below.

Referring still to FIG. 5, now that an evenly heated, balanced, eye-shield has been achieved, a single channel PWM may be used as shown to vary the input current to achieve desired levels of power densities for the entire eye-shield. For example, if 50% power is desired evenly across the entire lens, then that may be accomplished with this embodiment of the invention by setting the single-channel PWM 502 to a 50% on, 50% off, setting. Thus, with this embodiment of the invention, multichannel PWM is not required to balance out the eye-shield regions, since this has been accomplished directly with the construction of the eye-shield and its heating elements. And, if on the other hand simply a full power application is preferable for a given eye-shield, the single channel PWM could simply be replaced with a single battery and an on/off switch for providing on/off of full power evenly across the entire lens with this embodiment of the invention.

Figure 6A:
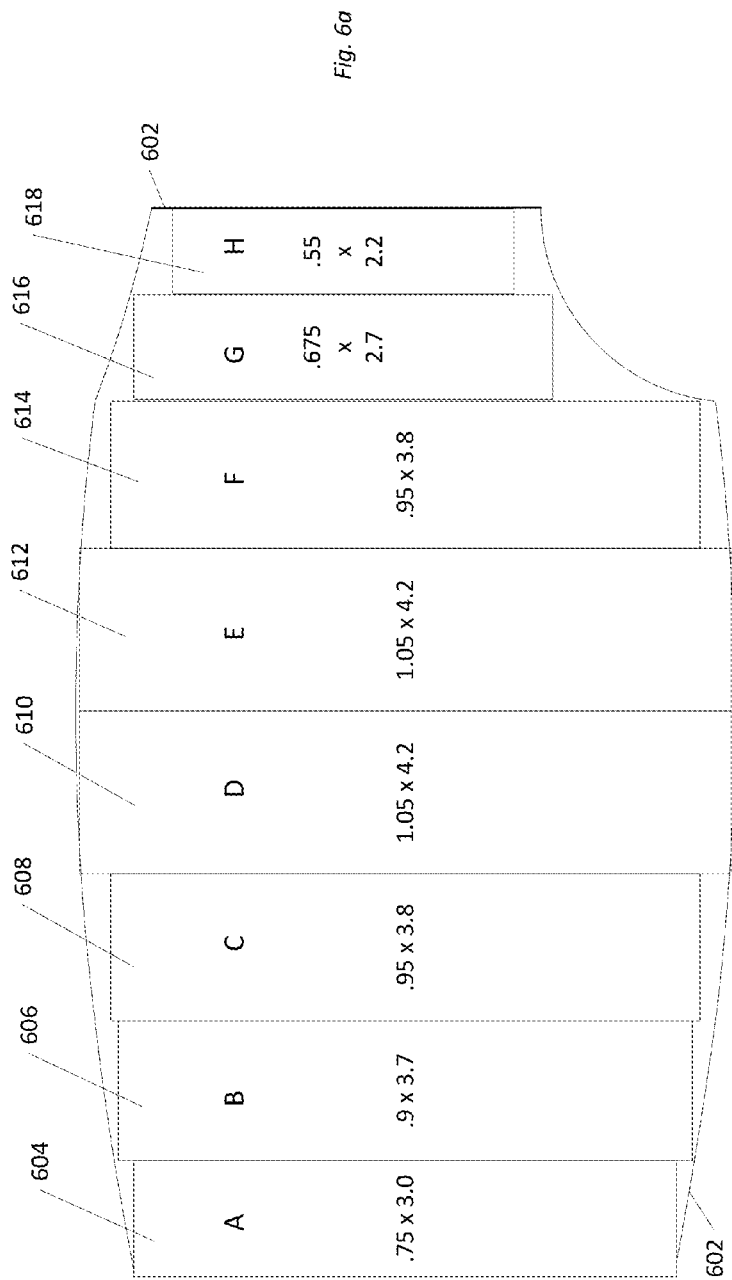
FIG. 6a is a graphic representation front view of another alternate embodiment of at least a portion of an eye-shield having a plurality of differently-sized (in plan view), electrically-isolated heating material regions on an irregular-shaped lens substrate and which may either have heating material regions of equal thickness or different thicknesses.

Referring now to FIG. 6a, an eye-shield substrate 602 is provided with even more electrically-isolated heating element regions A-H than in previous embodiments to enhance the degree to which the eye-shield may be controlled and further enhancing the degree to which even heating or custom heating may be accomplished across a still more irregularly-shaped eye-shield. Thus, there is provided as shown in FIG. 6a an eye-shield having eight heating element regions: A, B, C, D, E, F, G and H (604, 606, 608, 610, 612, 614, 616, 618, respectively) with size values as shown.

Figure 6B:
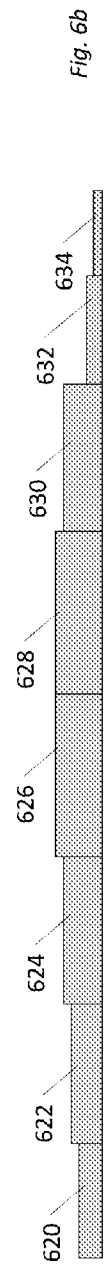
FIG. 6b is a graphic representation bottom view of the alternate embodiment of the portion of heated eye-shield shown in FIG. 6a (assuming varied thickness heating element regions in FIG. 6a), wherein even heating across the plurality of electrically-isolated heating element regions on the lens substrate is assumed and accomplished by applying different thicknesses of the same transparent thin-film conductive material to the lens substrate.

The resistivity of the heating element regions A-H of this embodiment of the invention have been normalized to provide even heating across the entire eye-shield substrate 602 either by using different thicknesses of heating element material (e.g., ITO) applied to the substrate as shown in FIG. 6b at 620, 622, 624, 626, 628, 630, 632, 634, or by using different resistivity formulations of heating material applied to the substrate (e.g., 10-ohm per square at 800 angstroms thick ITO, 20-ohm per square at 800 angstroms thick ITO, etc.). Finally, a combination of these methods may be employed. Note that a thicker application of the same ITO material tends to decrease the resistivity of the material on a region as compared to a thinner application.

Figure 6C:
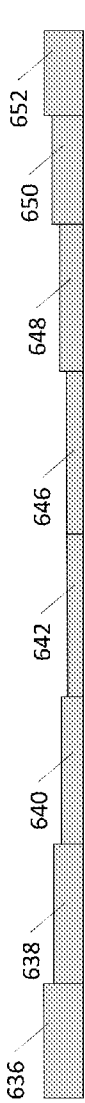
FIG. 6c is a graphic representation bottom view of the alternate embodiment of the portion of the heated eye-shield shown in FIG. 6a (assuming varied thickness heating element regions in FIG. 6a) wherein custom heating (i.e., cooler in the center and hotter at each end) across the plurality of electrically-isolated heating element regions on the lens substrate is assumed and accomplished by applying different thicknesses of the same transparent thin-film conductive material to the lens substrate.

Alternatively, the resistivity of the heating element regions A-H of this embodiment may be customized as shown in FIG. 6c to provide lesser heating in the center of the eye-shield (e.g., at regions C-F) and greater heating on the outside of the eye-shield (e.g., at regions A-B and G-H)—or according to some other custom profile. As shown in FIG. 6c, this is accomplished by changing the thickness of each region 636, 638, 640, 642, 644, 646, 648, 650, 652 of the eye-shield to vary the resistivity of that portion of the eye-shield. Alternatively, this may be accomplished by choosing different resistivity formulations of heating material applied to the substrate (e.g., 10-ohm per square at 800 angstroms thick ITO, 20-ohm per square at 800 angstroms thick ITO, etc.). Finally, a combination of these methods may be employed as well.

Thus, it may be appreciated that, whether an evenly-heated embodiment of the eye-shield is desired, or a customized heated embodiment of the eye-shield is desired, the desired result may be achieved by varying the resistivity of different segments of the eye-shield by varying the thickness, by choosing a different formulation of heating material, or by utilizing PWM heating channel technology as disclosed in the PWM Application.

Thus, the embodiment shown in FIG. 6a comprising regions A-H may have normalized, or equalized, R values to balance power densities as described above using, for example, one or both of formulation selection and thickness application of heating material. Accordingly, one advantage illustrated by the embodiment shown in FIG. 6a is that if, for example, a multichannel PWM heating source were to be used to vary the power density of the regions, the PWM system wouldn't have to compensate for undesirable hot spots because the lens has already been normalized. This, in turn allows for a greater range of control of the entire lens by the PWM, since part of the degree of adjustment available will not have been lost in compensating for overheating areas of the eye-shield. By way of example referring to FIG. 6a, it might be desirable to increase the number of regions to provide better granularity, or degree, of control of the heated areas on the eye-shield as shown with varying resistivity values calculated (and able to be achieved as described above) as follows:

A: $R=(E^2/Pd)/H^2$ adding values: $R=(8.4^2/0.2)/3^2=39.2$
B: $R=(E^2/Pd)/H^2$ adding values: $R=(8.4^2/0.2)/3.7^2=25.8$
C: $R=(E^2/Pd)/H^2$ adding values: $R=(8.4^2/0.2)/3.8^2=24.4$
D: $R=(E^2/Pd)/H^2$ adding values: $R=(8.4^2/0.2)/4.2^2=20.0$
E: $R=(E^2/Pd)/H^2$ adding values: $R=(8.4^2/0.2)/4.2^2=20.0$
F: $R=(E^2/Pd)/H^2$ adding values: $R=(8.4^2/0.2)/3.8^2=24.4$
G: $R=(E^2/Pd)/H^2$ adding values: $R=(8.4^2/0.2)/2.7^2=48.4$
H: $R=(E^2/Pd)/H^2$ adding values: $R=(8.4^2/0.2)/2.2^2=72.9$ The foregoing resistivity per square values are calculated for even heating across the entire substrate 602, and may be accomplished either by changing the effective voltage with PWM, or by changing the formulation or thickness of application of the heating material applied as described above. Further, it will be appreciated that the greater the specificity of regions, as for example shown and described in FIG. 8, the greater control over the lens that may be achieved and the greater the degree of evenness may be achieved across the entire lens.

Referring now to FIGS. 7a-7c there is provided part of an eye-shield substrate 702 having a plurality of contiguous heating element regions A-H (704, 706, 708, 710, 712, 714, 716, 718, respectively). Should a greater degree of even-heating specificity be desired on a given eye-shield, for example for a highly-irregularly shaped eye-shield, but for which nevertheless a simplified electronics system is desired, even as simple as a single battery, the invention includes an embodiment such as that of FIG. 7a wherein a single upper bus bar 754, and a single lower bus bar 756, may be used to connect with this plurality of contiguous heating element regions.

In FIG. 7b, a balanced heating eye-shield or screen is shown wherein, similarly to FIG. 6b, the even heating may be accomplished by one or a combination of varying the thickness of the heating material applied and selection of different formulations of heating material for different areas. However, varying the thickness of the heating material for the present embodiment is preferable, since in this way a smoother transitioning of variation of resistivity across the lens may be achieved without banding. Thus, FIG. 7b illustrates an evenly heating eye-shield comprising regions 720, 722, 724, 726, 728, 730, 732, 734, wherein the inner regions 724, 726, 728, 730 are thicker than the outer regions 720, 722, 732, 734 to provide normalized heating across the entire substrate similarly to that described previously in connection with FIG. 6b. However, as shown in FIG. 7b, the transitions between the contiguous segments or regions of heating material are smoother, less stair-stepped, allowing for less contrast between regions and thus smoother power density transitions between regions. In other words, the power densities of the contiguous embodiment of the eye-shield shown in FIG. 7b are continuously variable.

In FIG. 7c, there is shown a customized heated eye-shield having a plurality of contiguous heating elements 736, 738, 740, 742, 744, 746, 748, 750, 752 wherein, similarly to FIG. 6C, the custom heating profile provides for cooler segments in the middle areas 740, 742, 744, 746 and warmer regions in the outer areas 736, 738, 750, 752. As described in connection with FIG. 7b, the power density transitions with this embodiment are less stair-stepped and more continuously variable across the eye-shield, thus providing smoother power density transition between these contiguous regions. Also, as with the eye-shield of FIGS. 6a-6c and 7a-7b, the embodiment of the invention shown in FIG. 7c may be accomplished with a single power source, such as a single battery, or a single channel PWM, driving the single bus bars 754, 756.

The figures illustrating embodiments of the invention shown in FIGS. 6b, 6c, 7b and 7c are for illustrative purposes only. And while an attempt has been made to show relative differences in thickness of application of heating material to scale, it will nevertheless be appreciated that since these thickness are on the order of hundreds of angstroms thick, the drawings represent rough approximations of relative thickness of material, not actual to-scale representations.

Figure 8:
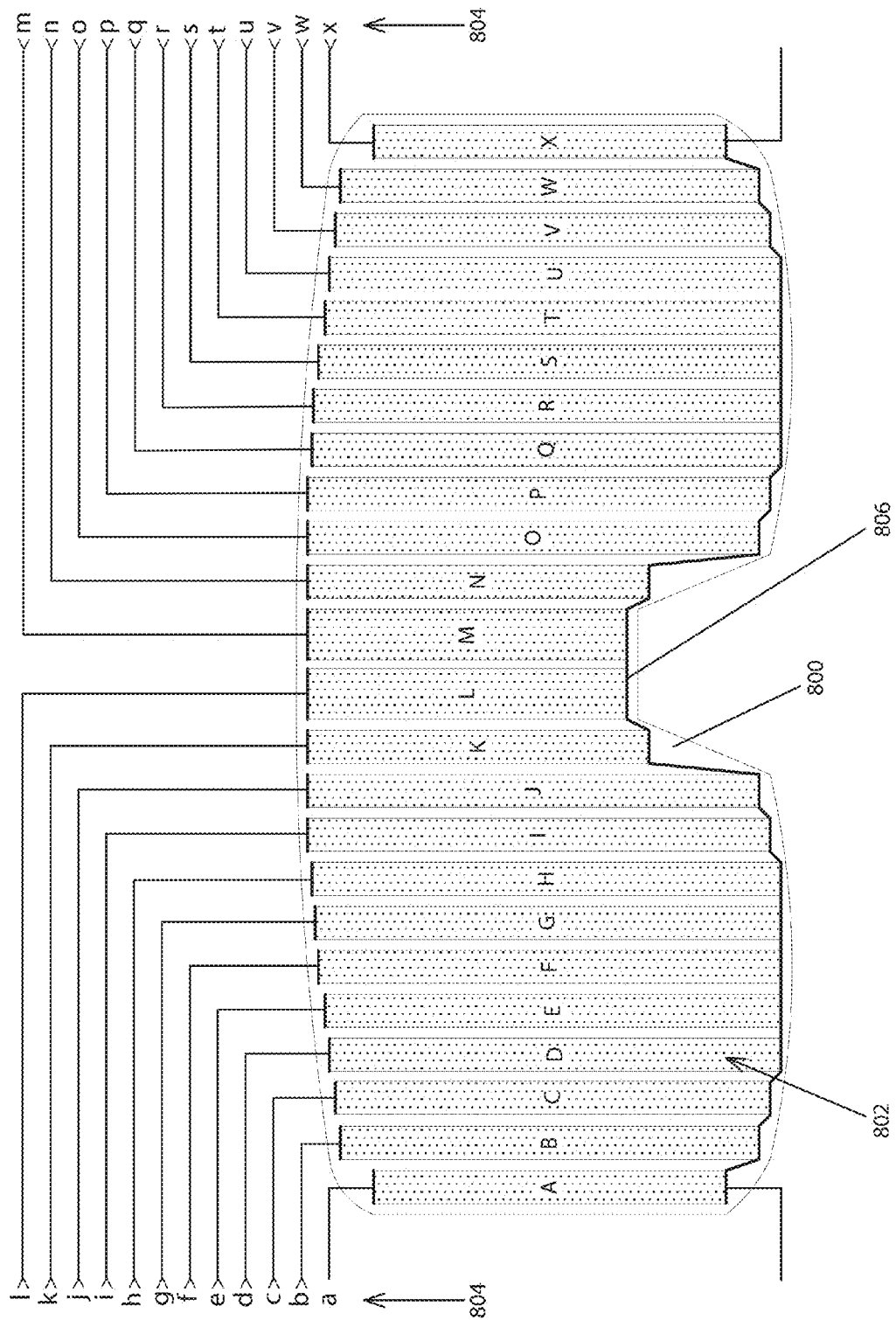
FIG. 8 is a schematic representation of another alternate embodiment of an eye-shield having a plurality of electrically-isolated heating material regions on an irregular-shaped lens substrate and using a plurality of upper bus bars, and a single lower ground bus bar, for connecting each of the heating material regions with a multichannel circuit, as with a multichannel PWM-controlled goggle circuit.

Referring now to FIG. 8, there is shown an eye-shield substrate 800 that is divided into even more, that is twenty four, heating regions, regions 802, A-X, than previously-described embodiments. Preferably each of these heating regions 802, A-X has been normalized as described above in that they either have even heating, or a desired custom profile. This embodiment of the invention clearly shows that over the bridge of the nose, the regions are less high (that is, they have a lesser value of H), and thus they would traditionally be prone to overheating without the present invention. Further, there are provided multiple channels a-x such that multiple PWM channels may be used, as described in the PWM Application, to further specify and drive the eye-shield heating system in a way that conserves battery life. Further, FIG. 8 illustrates the use of a plurality of bus bars, one for each channel to enable independent control of and power to each heating region 802, A-X, and a single ground bus bar 806.

Because of the greater specified granularity of control provided with the embodiment of the invention of FIG. 8, different detailed profiles may be implemented, all with the same eye-shield, as driven by a computer microprocessor contained within the goggle. Some examples of these profiles include a skier sunny-day profile, a snowboarder icing conditions profile, a rock climber raining conditions profile, a rescue patrol profile, a snowmobiler profile and a dive mask profile, etc.

While preferred embodiments of the present invention have been shown and described, it will be apparent to those skilled in the art that many changes and modifications may be made without departing from the invention in its broader aspects. For example, it will be appreciated that one of ordinary skill in the art may mix and match the various components of the various embodiments of the invention without departing from the true spirit of the invention as claimed. The appended claims are therefore intended to cover all such changes and modifications as fall within the true spirit and scope of the invention.

Figure 9:
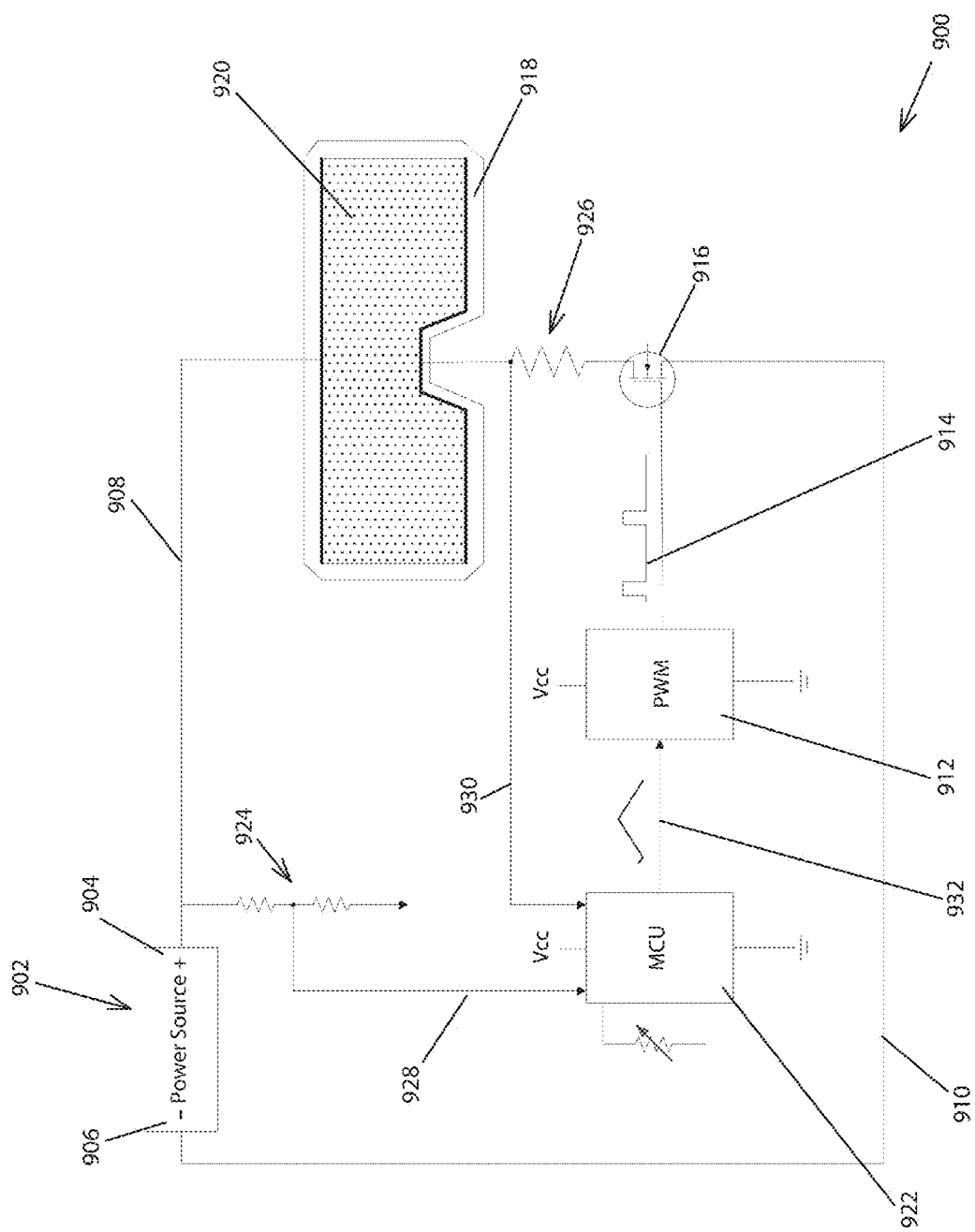
FIG. 9 is a schematic representation of an embodiment of a voltage and current sensing, single-pulse-width modulator (PWM), current adjusting, single-region eye-shield fog prevention system in accordance with an aspect of the invention.

Referring to FIG. 9, a single pulse-width modulator (PWM), single region fog prevention system 900 is shown comprising a battery power source 902 having positive and negative terminals 904, 906, circuit wires 908, 910, PWM 912 (which generates signal 914), MOSFET switch 916, eye-shield 918, heating element 920, a microcomputer (MCU) 922, a heater voltage sense resistor 924, a heater current sense resistor 926, a sense voltage 928, and a heater current voltage sense 930. A circuit 908, 910 interconnects the battery power source 902, the PWM 912, the MCU 922, the MOSFET switch 916, the heater current sense resistor 926, the sense voltage 928, the heater voltage sense resistor 924 and the heating element 920, the MCU 922 gathers information about the heater voltage sense resistor 924 and determines the heating element 920 resistance. The MCU 922 then relays information based on the heating element 920 resistance to the PWM 912 in order to adjust current which the PWM 912 controls. Controlling the current will in turn help to maintain temperature of the heating element 920 from one eye-shield defogging system 900 to another, despite variations in heating element resistivity from one eye-shield to the next, or from one eye-shield heating region to another, for example among regions A-H of FIG. 6a, regions A-H of FIG. 7a, or regions A-X of FIG. 8, to a temperature that is above an anticipated dew point temperature of an operating environment, despite variations in heating element resistivity from one region to the next.

Thus, although FIG. 9 is shown as a single PWM, single region fog prevention system, it will be appreciated that the invention may be applied to eye-shields having more than one region, as has been shown in FIGS. 2-8, where there is a progression of less complex to more complex embodiments of the invention having more than one region on the eye-shield, in order to create uniformity, or consistently accurate power densities for a custom heating profile, while heating each eye-shield region relative to each other eye-shield region, despite variations in resistivity of the heating elements of each of the regions. And, alternatively, the invention may be applied to ensure that multiple eye-shields have consistent properties as experienced by users from one eye-shield to another eye-shield, despite variations in resistivity of the heating elements on each of the eye-shields. It will be appreciated that there will be other combinations of the elements to form a heated eye-shield lens which would not depart from the scope and spirit of the invention as set forth in the claims portion of this specification.

In the embodiment of the invention shown in FIG. 9, the MCU 922 is shown as a device which comprises a potentiometer and has an internal reference voltage (vref) that is lower than the battery minimum usable voltage and provides an output voltage (input voltage to the PWM 912), the output voltage from the MCU 922 being some voltage between zero and the reference voltage (vref) based upon the setting of the potentiometer. Responsive to the MCU 922, the PWM 912 produces a corresponding percentage on/off signal that can be varied as a result of output from the MCU 922. In a preferred system using digital logic, a control MCU responsive to a MORE (increase) button and responsive to a LESS (decrease) button directly varies the duty cycle of the PWM 912 and thereby varies the amount of current delivered to the heating element 920 without requiring an intermediate voltage reference.

An output line 932 carrying the output voltage of the MCU 922 is operatively connected between the MCU 922 and the PWM 912. The PWM 912 translates the output voltage from the MCU 922 into a signal having a duty cycle corresponding and proportional to the magnitude of the voltage into the PWM 912. The duty cycle of the PWM's 912 output will therefore vary in relation to the voltage in from the MCU 922 such that a near-zero input voltage from the MCU 922 to the PWM 912 will result in a near-zero percent on/near 100 percent off duty cycle output of the PWM 912. By contrast, where the voltage in from the MCU 922 to the PWM 912 is near the maximum voltage (vref) of the MCU 922, a resulting near 100 percent on/near-zero percent off duty cycle output of the PWM would result. Further, and accordingly, for each intermediate setting of the MCU 922 between minimum and maximum output voltage to the PWM 912, a corresponding intermediate percentage on/percentage off duty cycle output of the PWM 912 would result. Thus, the MCU 922 enables varied output duty cycles of the PWM 912.

The defogging ability of the heating element 920 is determined by the amount of power supplied to the heating element 920. Heating element power is a function of the voltage applied across the heating element 920, the amount of time the voltage is applied to the heating element 920 which is established by the duty cycle of the PWM 912, and electrical resistance of the heating element 920. The heating element power is governed by the following equation:

$$\text{Heating Power} = \left(\frac{V^2}{R}\right)\left(\frac{\text{Duty Cycle}}{100}\right)$$

Where V is voltage, and R is heating element 920 resistance, and where duty cycle is expressed as a percent of switching element "on time". Therefore, as shown by this equation, actual heating power for heating element 920 in any given eye-shield 918 varies not just with voltage and duty cycle, but also with the resistance of heating element 920.

In order to maintain a consistent amount of power to the heating element 920 from one eye-shield to the next, and thus maintain a constant temperature of the heating element 920 from one eye-shield to the next, or one region of an eye-shield to another region of the same eye-shield, the duty cycle of the PWM 912 is increased or decreased to compensate for varying resistances of the heating element 920. In order to correctly compensate for variations of heating element 920 resistance, the MCU 922 must first establish the actual value of resistance of heating element 920. The MCU 922 first establishes the actual resistance by monitoring and obtaining values for the sense voltage 928 through the heater voltage sense resistor 924 that is applied to the heating element 920, and also monitoring the heater current sense voltage 930 that is applied through the heater current sense resistor 926 that has a fixed resistance. The MCU 922 will do this whenever the PWM 912 is in the "on" state.

After monitoring and obtaining a value for the sense voltage 928 and heater current sense voltage 930, and already knowing a value for the heater voltage sense resistor 924, the MCU 922 then uses these voltage values and resistance values to determine the heating element resistance using the following equation.

$$\text{Heating Element Resistance} = \frac{\text{Heater Current Sense Voltage 930}}{\left(\frac{\text{Sense Voltage 928}}{\text{Heater Voltage Sense Resistance 924}}\right)}$$

Now that the heating element resistance is known, the MCU 922 will relay a signal to the PWM to adjust the duty cycle by a multiplying factor, called a PWM adjustment factor. The PWM adjustment factor is derived from the heating element resistance that is calculated by the MCU 922 using the following equation:

$$PWM \text{ Adjustment Factor} = \frac{\text{Heating Element Resistance}}{\text{Nominal Resistance}}$$

where nominal resistance is a known and a desired value of resistance for the heating element 920.

In the instance of this MCU embodiment of the invention, a two-dimensional look-up table is employed, an example of which is seen in FIG. 10. The look-up table creates a mapping of PWM adjustment factors that relates to heating element resistance values. For example, in an eye-shield design where the nominal heating element 920 resistance is ten ohms, where also there is a known variation of resistance from one eye-shield to another eye-shield or one region of an eye-shield to another region of the same eye-shield of plus or minus twenty percent, then a look-up might look as it appears in FIG. 10. Thus, if it is determined by an MCU 922 of the system of the invention that the heating element's 920 resistance is eight ohms, instead of the specified ten ohms, the system would compensate for the variance by supplying a PWM adjustment factor of 0.80 as described previously in connection with the look-up table of FIG. 10. On the other hand, a heating element 920 resistance of twelve ohms would be compensated by the system with a PWM adjustment factor of 1.20. In this example of a two-dimensional look-up table as shown in FIG. 10, the nominal value of the heating element 920 resistance is ten ohms. However, other nominal resistances and measured resistance ranges can be used, and PWM adjustment factors corresponding to other nominal resistances and measured resistance ranges are found using the equation for PWM adjustment factors.

In the two-dimensional look-up table as shown in FIG. 10, the number of heating element resistances expressed in the table is variable, and is dependent upon the specificity with which PWM 912 adjustments should be made for a given application. It might be desirable in some circumstances to have a fine granularity of PWM adjustments so that the heating element 920 stays at a precise temperature. In another circumstance, a broad granularity of PWM adjustments might be more suitable when consistent temperature is not necessary. In all circumstances, this combination of heating element 920 resistance sensing and corresponding PWM 912 duty cycle adjustment allows the eye-shield heating element 920 to maintain constant heat, and the ability to compensate for variations in resistance encountered from one eye-shield region to another, and one eye-shield to another eye-shield as may be determined, for example, by testing resistivity of a batch of eye-shields.

While a preferred embodiment of the present invention has been shown and described, as well as other embodiments of the invention, it will be apparent to those skilled in the art that many changes and modifications may be made without departing from the invention in its broader aspects. For example, it will be appreciated that one of ordinary skill in the art may mix and match various components of the embodiments of the invention shown and described without departing from the true spirit of the invention as claimed. The appended claims are therefore intended to cover all such changes and modifications as fall within the true spirit and scope of the invention.

The invention claimed is:

1. An eye-shield condensation prevention system comprising:
   an eye-shield adapted for protecting a user's eyes, said eye-shield having a surface area divisible into at least one region for facilitating region heating of said eye-shield to a desired temperature;
   a power source;
   at least one pulse-width modulator;
   at least one microcomputer;
   at least one heating element on and corresponding with the at least one region for facilitating region heating of said eye-shield, said at least one heating element operatively connected to and corresponding with said at least one pulse-width modulator;
   a sensing circuit for comparing voltage sensed from said power source and heating element resistance voltage;
   and at least one circuit interconnecting said power source, said at least one pulse-width modulator, said at least one microcomputer, said at least one corresponding heating element for heating said eye-shield and said sensing circuit, wherein said at least one microcomputer relays information to said at least one pulse-width modulator that controls current to maintain the temperature of said at least one heating element region to a temperature above an anticipated dew point of an operating environment, said microcomputer determining heating element resistance from said sensing circuit and adjusting said pulse-width modulator's control of current to said heater to compensate for variations in resistance that might otherwise be encountered from at least one of one eye-shield region to another eye-shield region and one eye-shield to another eye-shield.

2. The eye-shield condensation prevention system of claim 1, wherein said eye-shield condensation prevention system comprises a plurality of pulse-width modulators corresponding to a plurality of eye-shield regions and a corresponding plurality of heating elements of a goggle lens, and wherein said eye-shield condensation prevention system is used to adjust at least one of said pulse-width modulators' control of current to a corresponding eye-shield region and heating element.

3. The eye-shield condensation prevention system of claim 1, wherein said eye-shield condensation system further comprises a look-up table of heating element resistance values each associated with a corresponding plurality of pulse-width adjustment factors to facilitate calculation by said microcomputer of an appropriate adjustment to be applied to said at least one pulse-width modulator to compensate for variations in resistance encountered.

4. The eye-shield condensation prevention system of claim 1, further comprising a plurality of eye-shield condensation prevention systems in accordance with claim 1, wherein a first of said eye-shield condensation prevention systems is used to enable pulse-width modulator duty cycle adjustments to maintain constant heat from at least one heating element of said first of said plurality of eye-shield condensation prevention systems relative to the at least one heating element of a second of said plurality of eye-shield condensation prevention systems, despite variations of heater resistance values from said first eye-shield condensation prevention system and said second eye-shield condensation prevention system.

* * * * *